(12) United States Patent
Zhou et al.

(10) Patent No.: US 6,737,427 B2
(45) Date of Patent: May 18, 2004

(54) MUCIN SYNTHESIS INHIBITORS

(75) Inventors: Yuhong Zhou, Dreshler, PA (US); Roy C. Levitt, Ambler, PA (US); Nicholas C. Nicolaides, Media, PA (US); Steve Jones, West Chester, PA (US); Mike McLane, Lansdale, PA (US)

(73) Assignee: Genaera Corporation, Plymouth Meeting, PA (US)

( * ) Notice: Subject to any disclaimer, the term of this patent is extended or adjusted under 35 U.S.C. 154(b) by 203 days.

(21) Appl. No.: 09/774,243

(22) Filed: Jan. 31, 2001

(65) Prior Publication Data
US 2001/0041685 A1 Nov. 15, 2001

Related U.S. Application Data

(60) Provisional application No. 60/252,052, filed on Nov. 20, 2000, provisional application No. 60/242,134, filed on Oct. 23, 2000, provisional application No. 60/230,783, filed on Sep. 7, 2000, provisional application No. 60/193,111, filed on Mar. 30, 2000, and provisional application No. 60/179,127, filed on Jan. 31, 2000.

(51) Int. Cl.[7] .................. A61K 31/517; A61K 31/549; A61K 31/443; A61K 31/195

(52) U.S. Cl. ................ 514/266.4; 514/223.2; 514/337; 514/567

(58) Field of Search ................ 514/266.4, 223.2, 514/337, 567

(56) References Cited

U.S. PATENT DOCUMENTS

| | | | | |
|---|---|---|---|---|
| 5,733,748 A | | 3/1998 | Yu | ........................ 435/70.1 |
| 5,875,776 A | | 3/1999 | Vaghefi | ................ 128/203.15 |
| 6,136,539 A | * | 10/2000 | Basbaum et al. | ............. 435/6 |
| 6,245,320 B1 | * | 6/2001 | Kim | ........................ 424/43 |

FOREIGN PATENT DOCUMENTS

| | | |
|---|---|---|
| WO | WO 96/39419 | 12/1996 |
| WO | WO 99/44620 | 9/1999 |

OTHER PUBLICATIONS

Aikawa et al. (1992) Marked goblet cell hyperplasic with mucus accumulation in the airways of patients who died of severe acute asthma attack, Chest 101:916–921.

Alexander et al. (1992) Trial of cyclosporin in corticosteroid–dependent chronic severe asthma, Lancet. 339:324–328.

Beasley et al. (1989) Cellular events in the bronchi in mild asthma and after bronchial provocation, Am. Rev. Respir. Dis. 139:806–817.

Borchers et al. (1999) Monocyte inflammation augments acrolein–induced Muc5ac expression in mouse lung, Am. J. Physiol. 277:L489–L497.

Bousquet et al. (1990) Eosinophilic inflammation in asthma, N. Engl. J. Med. 323:1033–1039.

Burrows et al. (1989) Association of asthma with serum IgE levels and skin–test reactivity to allergens, N. Eng. J. Med. 320:271–277.

Cardell et al. (1959) Death in asthmatics, Thorax. 14:341–352.

Chaumeil (1998) Micronization: a method of improving the bioavailability of poorly soluble drugs, Meth. Find. Exp. Clin. Pharmacol. 20:211–215.

Chu et al. (1992) Glycophorin A interacts with interleukin–2 and inhibits interleukin–2–dependent T–lymphocyte proliferation, Cell. Immunol. 145:223–239.

Clifford et al. (1987) Symptoms, atopy and bronchial response to methacholine in parents with asthma and their children, Arch. Dis. Childhood 62:66–73.

Cunningham et al. (1995) Cloning of an epithelial chloride channel from bovine trachea, J. Biol. Chem. 29:31016–31026.

Cutz et al. (1978) Ultrastructure of airways in children with asthma, Histopathology 2:407–421.

Dong et al. (1999) IL–9 induces chemokine expression in lung epithelial cells and baseline airway eosinophilia in transgenic mice, Eur. J. Immunol. 29:2130–2139.

Doucet et al. (1998) Interleukin (IL) 4 and IL–13 act on human lung fibroblasts. Implication in asthma, J. Clin. Invest. 101:2129–2139.

Doull et al. (1996) Allelic association of gene markers on chromosomes 5q and 11q with atopy and bronchial hyper–responsiveness, Am. J. Respir. Crit. Care Med. 153:1280–1284.

Dugas et al. (1993) Interleukin–9 potentiates the interleukin–4–induced immunoglobulin (IgG, IgM and IgE) production by normal human B lymphocytes, Eur. J. Immunol. 23:1687–1692.

Dunnill et al. (1969) A comparison of the quantitative anatomy of the bronchi in normal subjects, in asthmaticus, in chronic bronchitis, and in emphysema, Thorax 24:176–179.

Earle et al. (1953) Fatal bronchial asthma, Thorax. 8:195–206.

Eklund et al. (1993) Induction by IL–9 and suppression by IL–3 and IL–4 of the levels of chromosome 14–derived transcripts that encode late–expressed mouse mast cell proteases, J. Immunol. 151:4266–4273.

(List continued on next page.)

Primary Examiner—James O. Wilson
Assistant Examiner—Howard V. Owens
(74) Attorney, Agent, or Firm—Morgan, Lewis & Bockius LLP

(57) ABSTRACT

The claimed invention relates to methods of modulating mucin synthesis and the therapeutic application of compounds in controlling mucin over-production associated with diseases such as chronic obstructive pulmonary diseases (COPD) including asthma and chronic bronchitis, inflammatory lung diseases, cystic fibrosis and acute or chronic respiratory infectious diseases.

59 Claims, 20 Drawing Sheets

OTHER PUBLICATIONS

Eng et al. (1996) Short–term efficacy of ultrasonically nebulized hypertonic saline in cystic fibrosis, Pediatr. Pulmonol. 21:77–83.

Ewart et al. (1995) Respiratory system mechanics in mice measured by end–inflation occlusion, J. Appl. Phys. 79:560–566.

Gergen et al. (1992) The increasing problem of asthma in the United States, Am. Rev. Respir. Dis. 146:823–824.

Gergen et al. (1991) The association of allergen skin test reactivity and respiratory disease among whites in the U.S. population, Arch. Intern. Med. 151:487–492.

Glynn et al. (1960) Bronchial biopsy in chronic bronchitis and asthma, Thorax 15:142–153.

Halonen et al. (1992) The predictive relationship between serum IgE levels at birth and subsequent incidences of lower respiratory illnesses and eczema in infants, Am. Rev. Respir. Dis. 146:866–870.

Holgate et al. (1999) The bronchial epithelium as a key regulator of airway inflammation and remodeling in asthma, Clin. Exp. Allergy 29:90–95.

Jeffery et al. (1991) Morphology of the airway wall in asthma and in chronic obstructive pulmonary disease, Am. Rev. Respir. Dis, 143:1152–1158.

Kleeberger et al. (1990) A genetic model for evaluation of susceptibility to ozone–induced inflammation, Am. J. Physiol. 258:L313–L320.

Kreitman et al. (1994) Site–specific conjugation to interleukin 4 containing mutated cysteine residues produces interleukin 4–toxin conjugates with improved binding and activity, Biochem. 33:11637–11644.

Levitt et al. (1995) Genetic susceptibility to atracurium–induced bronchoconstriction, Am. J. Respir. Crit. Care. Med. 151:1537–1542.

Levitt et al. (1989) Autosomal recessive inheritance of airway hyper–reactivity to 5–hydroxytryptamine, J. Appl. Physiol. 67:1125–1132.

Levitt et al. (1988) Expression of airway hyper–reactivity to acetylcholine as a simple autosomal recessive trait in mice, FASEB J. 2:2605–2608.

Levitt (1991) Understanding biological variability in susceptibility to respiratory disease, Pharmacogenetics 1:94–97.

Li et al. (1998) Activation of NF–kappaB via a Src–dependent Ras–MAPK–pp90rsk pathway is required f r *Pseudomonas aeruginosa*–induced mucin overproduction in epithelial cells, Proc. Natl. Acad. Sci. USA 95:5718–5723.

Louahed et al. (1995) IL–9 induces expression of granzymes and high affinity IgE receptor in murine T helper clones, J. Immunol. 154:5061–5070.

Louahed et al. (2000) Interleukin–9 upregulates mucus expression in the airways, Am. J. Respir. Cell Mol. Biol. 22:649–656.

Marsh et al. (1982) The epidemiology and genetics of atopic allergy, New Eng. J. Med. 305:1551–1559.

McLane et al. (1998) Interleukin–9 promotes allergen–induced eosinophilic inflammation and airway hyperresponsiveness in transgenic mice, Am. J. Respir. Cell Mol. Biol. 19:713–720.

McLane et al. (2000) Lung delivery of an Interleukin–9 antibody treatment inhibits airway hyper–responsiveness (AHR), BAL eosinophilia, mucin production and serum IgE elevation to natural antigens in a murine model of asthma, Abstract for AAAAI meeting: Mar. 3–Mar. 8, 2000 in San Diego, CA and for ATS/ALA meeting: May 5, 2000 in Toronto, Canada.

Nguyen et al. (1998) Secretory effects of ATP on nontransformed dog pancreatic duct epithelial cells, Am. J. Physiol. 275:G104–G113.

Nicolaides et al. (1997) Interleukin 9: a candidate gene for asthma, Proc. Natl. Acad. Sci. USA 94:13175–13180.

Paillasse (1989) The relationship between airway inflammation and bronchial hyperresponsiveness, Clin. Exp. Allergy 19:395–398.

Petit–Frere et al. (1993) Interleukin–9 potentiates the interleukin–4–induced IgE and IgG1 release from murine B lymphocytes, Immunology 79:146–151.

Polito et al. (1998) Epithelial cells as regulators of airway inflammation, J. Allergy Clin. Immunol. 102:714–718.

Salvato (1968) Some histologic changes in chronic bronchitis and asthma, Thorax, 23:168–172.

Sears et al. (1991) Relation between airway responsiveness and serum IgE in children with asthma and in apparently normal children, N. Engl. J. Med. 325:1067–1071.

Shinogi et al. (2001) Quantitative analysis of mucin and lectin in maxillary sinus fluids in patients with acute and chronic sinusitis, Laryngoscope 111:240–245.

Takahashi et al. (1998) Effects of SS320A, a new cysteine derivative, on the change in the number of goblet cells induced by isoproterenol in rat tracheal epithelium, Jpn. J. Pharmacol. 77:71–77.

Temann et al. (1998) Expression of interleukin 9 in the lungs of transgenic mice causes airway inflammation, mast cell hyperplasia, and bronchial hyperresponsiveness, J. Exp. Med. 188:1307–1320.

Voynow et al. (1994) Quantitation of mucin mRNA in respiratory and intestinal epithelial cells, Am. J. Respir. Cell Mol. Biol. 11:742–750.

Voynow et al. (1999) Neutrophil elastase increases MUC5AC mRNA and protein expression in respiratory epithelial cells, Am. J. Physiol. 276:L835–L843.

Zav'yalov et al. (1992) Nonapeptide corresponding to the sequence 27–35 of the mature human IL–2 efficiently competes with rIL–2 for binding to thymocyte receptors [corrected], Immunol. Lett. 31:285–288.

Search report for International Application PCT/US01/03078.

* cited by examiner

MUCIN SYNTHESIS INHIBITORS

CROSS-REFERENCE TO RELATED APPLICATIONS

This application claims the benefit of U.S. Provisional Application No. 60/179,127, filed on Jan. 31, 2000, Provisional Application No. 60/193,111, filed on Mar. 30, 2000, Provisional Application No. 60/230,783, filed Sep. 7, 2000, Provisional Application No. 60/242,134 filed Oct. 23, 2000 and Provisional Application No. 60/252,052 filed Nov. 20, 2000 all of which are herein incorporated by reference in their entirety. All of the above referenced applications are entitled "Mucin Synthesis Inhibitors" and the inventors are Yuhong Zhou, Roy C. Levitt, Nicholas C. Nicolaides, Steve Jones, and Mike McLane.

This invention is also related to the subject matter of U.S. patent application Ser. No. 08/702,110, filed on Aug. 23, 1996, issued on Mar. 14, 2000, as U.S. Pat. No. 6,037,149 and is related to U.S. patent application Ser. No. 09/325,571, filed on Jun. 9, 1999 and U.S. Pat. No. 5,908,839 issued Jun. 1, 1999 all of which are all herein incorporated by reference in their entirety. In addition, this application is related to U.S. patent application Ser. No. 08/980,872, filed Dec. 1, 1997, which is herein incorporated by reference in its entirety.

FIELD OF THE INVENTION

This invention relates to methods of modulating mucin synthesis and the therapeutic application of compounds in controlling mucin over-production associated with diseases such as asthma, chronic bronchitis, inflammatory lung diseases, cystic fibrosis and acute or chronic respiratory infectious diseases as well as chronic obstructive pulmonary diseases (COPD).

BACKGROUND OF THE INVENTION

The airway epithelium is known to play an integral role in the airway defense mechanism via the mucociliary system and mechanical barriers. Recent studies indicate that airway epithelial cells (AEC) can be activated to produce and release biological mediators important in the pathogenesis of multiple airway disorders (Polito and Proud, 1998; Takizawa, 1998). Evidence has shown that the epithelium is fundamentally disordered in chronic airway disorders such as asthma, chronic bronchitis, emphysema, and cystic fibrosis (Holgate et al., 1999; Jeffery P K, 1991; Salvato, 1968; Glynn and Michaels, 1960). One of the hallmarks of these airway disorders is the over-production of mucus by AEC. The major macromolecular components of mucus are the large glycoproteins known as mucins. Recently, the molecular structure of at least 7 human mucins was determined. The known mucin transcripts are heterogeneous with no sequence homology between the genes (Voynow and Rose, 1994), yet they are similar in their overall repetitive structure.

Deleterious stimuli are known to activate AEC. These stimuli can vary from antigens in allergic disease to drugs or environmental pollutants, tobacco smoke, and infectious agents associated with forms of chronic obstructive pulmonary disease. AEC activation leads to altered ion transport, changes in ciliary beating, and the increased production and secretion of mucins leading to increased mucus. The mediators produced in response to AEC activation include chemokines that promote the influx of inflammatory cells (Takizawa, 1998). These inflammatory cells can in turn produce mediators that may injure AEC. AEC injury stimulates cellular proliferation (goblet cell and submucosal gland cell hyperplasia) that results in an expanded and continuous source of pro-inflammatory products, including proteases as well as growth factors that drive airway wall remodeling that can lead to lung destruction and the loss of function (Holgate et al., 1999).

The over-production of mucus and alteration of its physiochemical characteristics can contribute to lung pathology in a number of ways. Disruption of physiologic mucociliary clearance by the over-production of mucins can lead to mucus plugging, air trapping, and atelectasis which is often complicated by infection.

Asthma is a chronic obstructive lung disorder that appears to be increasing in prevalence and severity (Gergen and Weiss, 1992). It is estimated that 30–40% of the population suffers with atopic allergy and 15% of children and 5% of adults in the population suffer from asthma (Gergen and Weiss, 1992).

In asthma, activation of the immune system by antigens leads to allergic inflammation. When this type of immune activation occurs it is accompanied by pulmonary inflammation, bronchial hyperresponsiveness, goblet cell and submucosal gland hyperplasia, and mucin over-production and hyper-secretion (Basle et al., 1989) (Paillasse, 1989) (Bosque et al., 1990). Mucus over-production and plugging associated with goblet cell and submucosal gland cell hyperplasia is an important part of the pathology of asthma and has been described on examination of the airways of both mild asthmatics and individuals who have died with status asthmaticus (Earle, 1953) (Cardell and Pearson, 1959) (Dunnill, 1960) (Dunnill et al, 1969) (Aikawa et al., 1992) (Cutz et al., 1978). Certain inflammatory cells are important in this reaction including T cells, antigen presenting cells, B cells that produce IgE, basophils that bind IgE, and eosinophils. These inflammatory cells accumulate at the site of allergic inflammation and the toxic products they release contribute to the destruction of AEC and other tissues related to these disorders.

In the related patent applications mentioned above, applicants have demonstrated that interleukin-9 (IL9), its receptor and activities effected by IL9 are the appropriate targets for therapeutic intervention in atopic allergy, asthma and related disorders. Mediator release from mast cells by allergen has long been considered a critical initiating event in allergy. IL9 was originally identified as a mast cell growth factor and it has been demonstrated that IL9 up-regulates the expression of mast cell proteases including MCP-1, MCP-2, MCP-4 (Eklund et al., 1993) and granzyme B (Louahed et al., 1995). Thus, IL9 appears to serve a role in the proliferation and differentiation of mast cells. Moreover, IL9 up-regulates the expression of the alpha chain of the high affinity IgE receptor (Dugas et al., 1993). Furthermore, both in vitro and in vivo studies have shown IL9 to potentiate the release of IgE from primed B cells (Petit-Frere et al., 1993).

Recently, IL9 was shown to stimulate mucin synthesis and may account for as much as 50–60% of the mucin-stimulating activity of lung fluids in allergic airway disease (Longpre et al., 1999). A gross up-regulation of mucin synthesis and mucus over-production occurs in IL9 transgenic mice as compared to mice from the background strain. IL9 specifically up-regulates the MUC2 and MUC5AC genes and proteins in vitro and in vivo (Louahed et al, 2000). Moreover, IL9 neutralizing antibody inhibits completely the up-regulation of mucins in response to antigen challenge in animal models of asthma (McLane et al., 2000)

Current asthma treatments suffer from a number of disadvantages. The main therapeutic agents, beta-receptor agonists, reduce the symptoms thereby transiently improving pulmonary function, but do not affect the underlying inflammation nor do they suppress mucin production. In addition, constant use of beta-receptor agonists results in desensitization, which reduces their efficacy and safety (Molinoff et al., 1995). The agents that can diminish the underlying inflammation, and thereby decrease mucin production, such as anti-inflammatory steroids, have their own list of disadvantages that range from immunosuppression to bone loss (Molinoff et al., 1995).

Chronic bronchitis is another form of chronic obstructive pulmonary disorder. Nearly 5% of adults suffer with this pulmonary disorder. Chronic bronchitis is defined as the chronic over-production of sputum. Mucus over-production is generally associated with inflammation of the conducting airways. The mediators of inflammatory cells including neutrophils and macrophages may be associated with increased mucin gene expression in this disorder (Voynow et al., 1999; Borchers et al., 1999). The increased production of mucus is associated with airway obstruction, which is one of the cardinal features of this pulmonary disorder. Therapy is largely symptomatic and focused on controlling infection and preventing further loss of lung function. Decongestants, expectorants and combinations of these agents that are often used to treat the symptoms of bronchitis are not thought to alter mucin production. Mucolytics may promote mucociliary clearance and provide symptomatic relief by reducing the viscosity and/or the elasticity of the airway secretions but do not inhibit mucin synthesis or mucus over-production. (Takahashi et al., 1998

Cystic fibrosis (CF) is yet another disease that effects the lung and is associated with thick secretions resulting in airway obstruction and subsequent colonization and infection by inhaled pathogenic microorganisms (Eng et al., 1996). DNA levels are increased significantly in CF lung and can increase the viscosity of sputum. While recombinant aerosolized DNAse is of value in these patients, there is no effective treatment for the pathologic mucus over-production., Thus, there is a specific unmet need in the art for the identification of agents capable of inhibiting mucin over-production by airway epithelial cells in CF. In addition to the airway obstruction caused by mucin secretions, CF patients also suffer from mucus plugging in the pancreatic ducts which prevent the delivery of digestive enzymes to the GI tract. The result is malabsorption syndrome, steatorrhea and diarrhea.

While mucus over-production is one of the hallmarks of multiple chronic obstructive lung disorders, the art lacks any methods to block the synthesis or over-production of mucins associated with these pulmonary disorders. Thus, there is a specific need in the art to inhibit the over-production of mucins and thin the secretions of these patients to promote mucociliary clearance and preserve lung, function.

SUMMARY OF THE INVENTION

The current invention relates to the discovery of agents that inhibit the synthesis and over-production of mucin glycoproteins and methods of using these molecules to treat the pathologic over-production of mucus in chronic obstructive pulmonary disorders and other diseases.

In one aspect, the present invention provides a method of treating a subject with a respiratory disease characterized by the production of mucin, comprising administering to the subject an effective amount of a composition comprising at least one compound that decreases mucin synthesis or levels in the lungs or in the GI tract. In some embodiments, the mucin synthesis may be chloride channel dependent. In some embodiments, the compound decreases mucin synthesis in cells that express an ICACC chloride channel. In some embodiments, the compound is selected from a group consisting of analogues and derivatives of anthranilic acid, analogues and derivatives of 2-amino-nicotinic acid, analogues and derivatives of 2-amino-phenylacetic acid, bendroflumethiazide, salts thereof and prodrugs thereof. In some preferred embodiments, the compound is selected from the group consisting of talniflumate, flufenamic acid, niflumic acid, mefenamic acid, salts thereof, derivatives thereof and prodrugs thereof. In some preferred embodiments, the compositions of the present invention comprise talniflumate, a talniflumate derivative, a salt thereof or a prodrug thereof.

In some embodiments, the compositions of the present invention may comprise at least one compound that decreases mucin synthesis or levels in the lungs or in the GI tract wherein the compound is a quinoline or quinoline derivative. In some embodiments, the compound may be a quinoline modified with an amine group, preferably at the 2 or 3 position of the quinoline. In a preferred embodiment, the compound may be a 3-amino-quinoline in which the exocyclic nitrogen is modified with one or more moieties. In some embodiments, the exocyclic amine group may be modified with an aromatic moiety. The aromatic moiety may be modified or unmodified. In a preferred embodiment, the aromatic group is a benzyl group which may be modified with one or more substituents. Suitable substituents include, but are not limited to, halogens. In a preferred embodiment, the compound is an N-(fluorobenzyl)-3-amino-quinoline (FIG. 19), preferably the fluorine is in the meta position.

In another aspect of the present invention the compounds that decrease mucin synthesis are also inhibitors of the enzyme cyclooxygenase such as talniflumate. In a more preferred embodiment the compounds are specific inhibitors of the enzyme cyclooxygenase-2.

In another embodiment, the present invention provides a method of treating a subject with a respiratory disease characterized by the production of mucin by administering the compositions of the invention by inhalation. In some embodiments, the composition is in the form of a liquid or in the form of a powder. In some embodiments, the composition is aerosolized. In other embodiments, the composition further comprises at least one expectorant, antihistamine, mucolytic agent, antibiotic or decongestant agent. In some embodiments, the expectorant is guaifenesin. The compositions of the invention may further comprise at least one stabilizing agent, absorption-enhancing agent or flavoring agent. In some preferred embodiments, the stabilizing agent is cyclodextran and/or the absorption-enhancing agent is chitosan.

In some preferred embodiments, the compositions and methods of the present invention may be used to treat a respiratory disease selected from the group consisting of a chronic obstructive pulmonary disease (COPD), an inflammatory lung disease, cystic fibrosis and an acute or chronic infectious disease. The treatment of any one of these diseases may be by administering one or more of the compositions of the invention via inhalation. In some embodiments, the composition is administered via inhalation to the lungs. In preferred embodiments, the present invention provides methods and materials to treat a COPD selected from the group consisting of emphysema, chronic bronchitis and asthma.

In another preferred embodiment, the compositions and methods of the present invention may be used to treat the GI complications of cystic fibrosis such as malabsorption syndrome, steatorrhea and diarrhea. The treatment of this disease may be by administering one or more of the compositions of the invention orally.

In another embodiment, the present invention provides a therapeutic composition formulated for inhalation delivery comprising an amount effective to decrease mucin production or levels of at least one compound selected from the group consisting of talniflumate, flufenamic acid, niflumic acid, mefenamic acid, salts thereof, derivates thereof and prodrugs thereof. In some preferred embodiments, the composition comprises talniflumate, a talniflumate derivative, a salt thereof or a prodrug thereof. In some embodiments, the composition is in the form of a liquid or in the form of a powder. In some embodiments, the composition further comprises at least one expectorant, mucolytic agent, antibiotic, anti-histamine or decongestant agent. In some embodiments, the expectorant is guaifenesin.

In addition to the agents described above, the pharmaceutical compositions of the present invention formulated for inhalation may further comprise at least one stabilizing agent, absorption-enhancing agent or flavoring agent. In some embodiments, the stabilizing agent is a cyclodextran and/or the absorption-enhancing agent is chitosan.

The present invention also provides an inhalation device comprising a therapeutic composition as described above.

BRIEF DESCRIPTION OF THE FIGURES

FIG. 15A shows a section of lung (stained with H&E) from a mouse sensitized to *Aspergillus fumigatus* and allowed access to regular mouse chow.

DETAILED DESCRIPTION OF THE INVENTION

Figure 1:
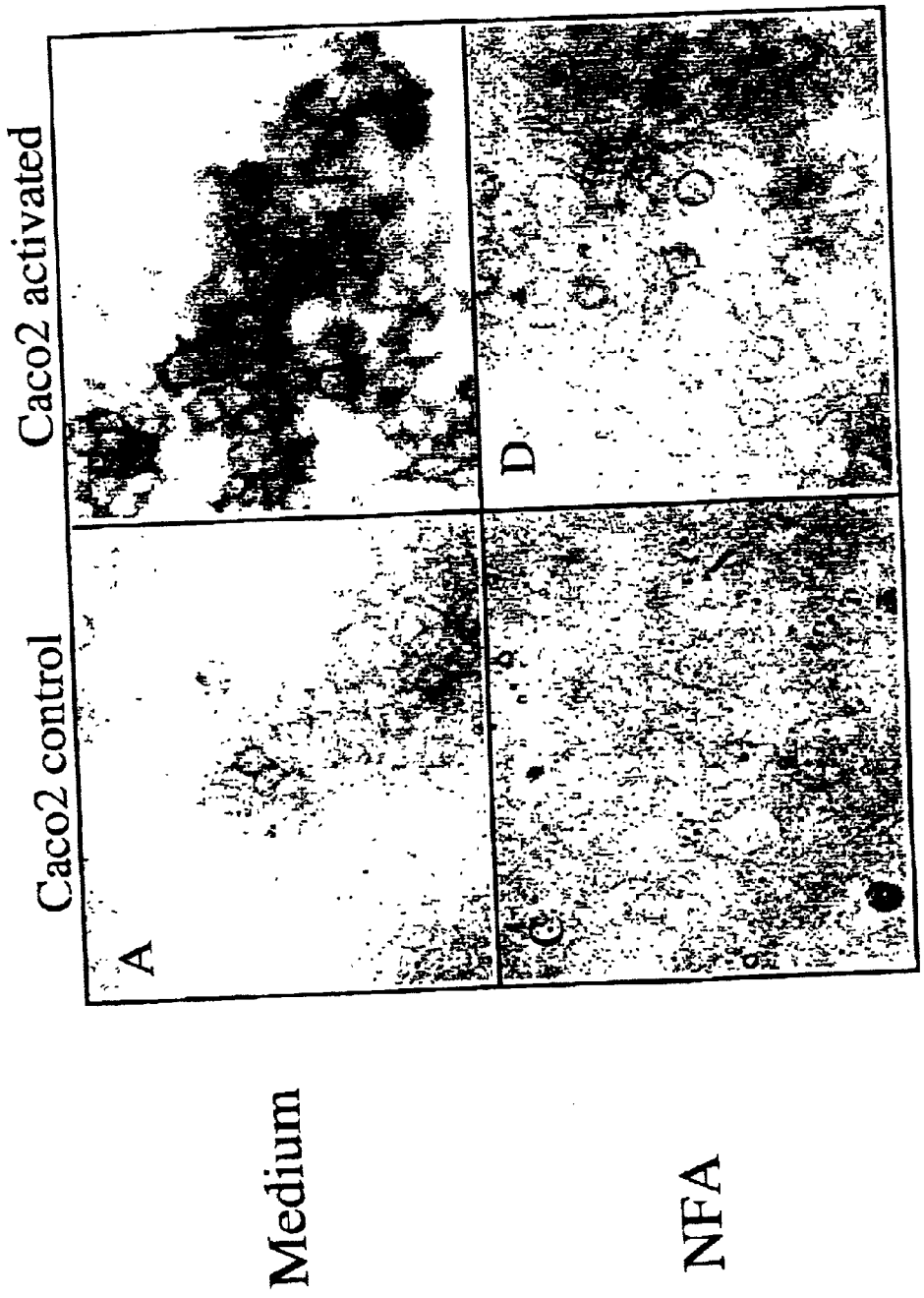
FIG. 1 shows the effect of NFA on mucin production. NFA inhibitor blocks mucin overproduction in vitro.

The present invention is, in part, derived from the finding that mucus over-production resulting from activation of nonciliated epithelial cells of the lung is caused by induction of mucin genes including MUC2 and MUC5AC. Thus, one aspect of the invention is the inhibition of epithelial cell activation. This inhibition of AEC activation down-regulates chemokine production, bronchial responsiveness, and mucin gene expression. Molecules that decrease mucin synthesis or levels are therefore part of the invention.

Agents that Decrease Mucin Synthesis or Levels

As described herein, the formulations and compositions of the invention include agents that decrease mucin synthesis or levels, or decrease in some way the over-production of mucin. As used herein, "decrease" is defined as a down-regulation in the level, activation, function, stability, or synthesis of mucin. Preferred agents decrease the chloride channel dependent level, activation, function, stability, or synthesis of mucin. As used herein, "chloride channel" refers to, but is not limited to, the ICACC chloride channel and the related channels referred to in WO 99/44620, which is herein incorporated by reference in its entirety. Agents that fall under these definitions may be identified or their activity verified by screening in the assays described in the Examples. For instance, the in vitro and in vivo assays described in Examples 7 and 8 may be used to screen, identify or verify an agent's activity.

Molecules that decrease mucin synthesis or levels include analogues and derivatives of anthranilic acid (2-aminobenzoic acid). In some preferred embodiments, the molecule may be an N-derivatized anthranilic acid. In some embodiments, the amino group of anthranilic acid may be modified with one or more groups. In some embodiments, the group may be an aromatic group. In a preferred embodiment, the group may be a trifluoromethyl-phenyl group preferably a 3-trifluoromethyl-phenyl group and the molecule that decreases mucin synthesis or levels is flufenamic acid. In another preferred embodiment, the amino group may be derivatized with a 2,3-dimethyl-phenyl group and the molecule that decreases mucin synthesis or levels is mefenamic acid. Those skilled in the art will appreciate that other phenyl derivatives of anthranilic acid may be used in the present invention. In other preferred embodiments, the benzoic acid ring may include one or more substituents. In a preferred embodiment, both the benzoic acid ring and the amino group may be modified. Other preferred embodiments, include molecules having substituents on the benzoic acid ring and aromatic groups attached to the amino group.

In some embodiments, the molecules that decrease mucin synthesis include analogues and derivatives of 2-aminonicotinic acid. In some embodiments the exocyclic amino group may be modified to include one or more groups. In some preferred embodiments, the exocyclic amine group may be modified with an aromatic group. Suitable aromatic groups include, but are not limited to, a phenyl group, a modified phenyl group, a benzyl group, a modified benzyl group and the like. In a preferred embodiment, the aromatic group may be a 3-trifluoromethyl-phenyl group and the derivative of 2-amino-nicotinic acid is niflumic acid.

In some embodiments, the molecule that decreases mucin synthesis may be an analogue or derivative of 2-aminophenylacetic acid. In some embodiments, the amino group may be modified to include one or more groups. In some embodiments, the amino group may be modified with an aromatic group. Suitable aromatic groups include, but are not limited to, a phenyl group, a modified phenyl group, a benzyl group, a modified benzyl group and the like. In a preferred embodiment, the 2-amino-phenylacetic acid is N-modified with a 2,6-dichlorophenyl group and the molecule that decreases mucin synthesis or levels is talniflumate.

In some embodiments, the molecule that decreases mucin synthesis or levels may be bendroflumethiazide.

The present invention also contemplates the use of prodrugs of one or more of the above-mentioned molecules that decrease mucin synthesis or levels. As defined herein, a prodrug is a molecule that is administered in a form other than that described above and is converted in the body of the subject into the form described. Preferred prodrugs include, but are not limited to, prodrugs of fenamates. Some preferred prodrugs are esters of the acid form of the molecule that decreases mucin synthesis or levels. Preferred esters include, but are not limited to, esters of NFA, for example, the beta-morpholinoethyl ester, morniflumate, and the phthalidyl ester, talniflumate.

Uses for Agents that Modulate the Production of Mucin.

As provided in the Examples, agents that modulate, decrease or down-regulate the expression of mucin may be used to modulate biological and pathologic processes associated with mucin production.

Figure 10:
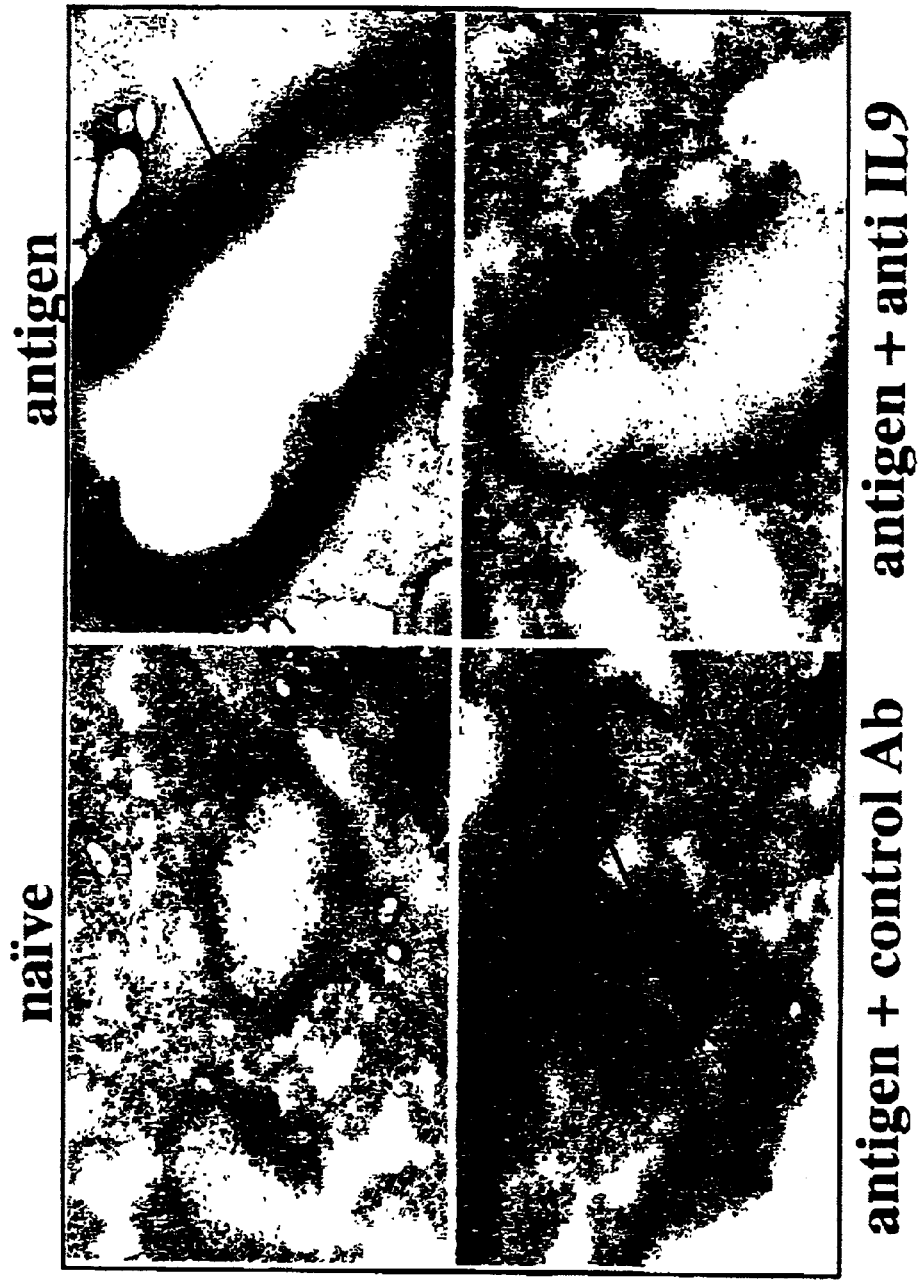
FIG. 10 shows the effect of anti-IL-9 antibody on mucin over-production in the lung of antigen-exposed mice. This figure shows neutralizing IL-9 antibody prevents mucin over-production in antigen-exposed mice.

Applicants have observed that IL9 selectively induces the expression of mucin gene products. Thus, the pleiotropic role for IL9, which is important to a number of antigen-induced responses, is dependent in part, on the up-regulation of mucin in AEC. When the functions of IL9 are down-regulated by neutralizing antibody treatment, animals can be completely protected from antigen-induced responses in the lung. These responses include: bronchial hyperresponsiveness, eosinophilia and elevated cell counts in bronchial lavage, elevated serum IgE, histologic changes in lung associated with inflammation, and goblet cell and submucosal gland cell hyperplasia associated with the over-production of mucus. The down-regulation of IL9 and asthmatic-like responses is associated with the down-regulated expression of mucin (FIG. 10). Thus, treatment of such responses, which underlie the pathogenesis of asthma and characterize allergic inflammation associated with this disorder, by down-regulating mucin production, is within the scope of this invention.

Histologic analysis of IL9 transgenic mice airways has shown mucin over-production in nonciliated epithelial cells (Temann et al., 1998; Louahed et al., 2000). Induction of mucin in the IL9 transgenic mouse lung suggests that IL9 promotes mucus production by these cells (see FIG. 8). Activated Caco2 cells that express the mRNA of MUC1, MUC2, MUC3, MUC4, MUC5B and MUC5AC have been produced and used to test for inhibitors of mucin production. These cells can be stained for mucin using Periodic Acid-Schiff staining (PAS). As shown in FIG. 1A, the untreated activated Caco2 cells stain intensely for PAS positive mucin glycoconjugates. Control and activated cells were cultured in the presence of niflumic acid (NFA) or 4,4'-diisothiocyanostilbene-2,2'-disulfonic acid (DIDS). PAS staining of inhibitor treated activated cells revealed significantly fewer positive staining glycoconjugates as compared with the untreated cells (FIG. 1D compared to 1B).

While a therapeutic potential for mucin down-regulation has been identified in asthma, Applicants have also recognized a therapeutic potential for down-regulation of mucin in cystic fibrosis. Patients with cystic fibrosis are hampered by lung disease characterized by thick secretions, which cause airway obstruction and subsequent colonization and infection by inhaled pathogenic microorganisms (Eng et al., 1996). Applicants therefore provide a method for treating cystic fibrosis by down regulating mucin production in the lung.

Mucin over production in cystic fibrosis is also present in the pancreatic ducts that deliver digestive enzymes to the GI tract resulting in malabsorption syndrome, steatorrhea and diarrhea. Applicants therefore also provide a method for treating cystic fibrosis by down regulating mucin production in the pancreas.

Applicants have also identified a therapeutic potential for mucin down-regulation in chronic bronchitis and emphysema. Patients with chronic bronchitis and emphysema are hampered by lung disease characterized by thick secretions, which cause airway obstruction and subsequent colonization and infection by inhaled pathogenic microorganisms (Eng et al., 1996). Applicants therefore provide a method for treating chronic bronchitis and emphysema by down regulating mucin production in the lung.

As used herein, a subject can be any mammal, so long as the mammal is in need of modulation of a pathological or biological process mediated by mucin production. The term "mammal" is meant as an individual belonging to the class Mammalia. The invention is particularly useful in the treatment of human subjects.

Pathological processes refer to a category of biological processes that produce a deleterious effect. For example, mucin over-production of the invention may be associated with respiratory disease, including chronic obstructive pulmonary disease (COPD), inflammatory lung disease, cystic fibrosis and an acute or chronic infectious disease. COPD includes, but is not limited to bronchitis, asthma and emphysema. Mucin over-production may also be associated with GI diseases such as malabsorption syndrome, steatorrhea and diarrhea that are present in cystic fibrosis.

As used herein, an agent is said to modulate a pathological process when the agent reduces the degree or severity of the process. For instance, airway obstruction may be prevented or disease progression modulated by the administration of agents that reduce or modulate in some way the synthesis, levels and/or over-production of mucin.

Therapeutic Compositions

The agents of the present invention can be provided alone, or in combination with other agents that modulate a particular pathological process. For example, an agent of the present invention can be administered in combination with anti-asthma agents. In another embodiment, an agent may be administered in combination with expectorants, mucolytics, antibiotics, antihistamines or decongestants. In still another embodiment, an agent may be administered along with a surfactant, a stabilizing agent, an absorption-enhancing agent, a beta adrenoreceptor or purine receptor agonist or a flavoring or other agent that increases the palatability of the compositions. As an example, compositions of the invention may contain, in addition to the active agent, an expectorant such as guaifenesin, a stabilizing agent such as cyclodextran and/or an absorption-enhancing agent such as chitosan. Any such agents may be used in the compositions of the invention.

As used herein, two or more agents are said to be administered in combination when the agents are administered simultaneously or are administered independently in a fashion such that the agents will act at the same time.

The agents of the present invention can be administered via parenteral, subcutaneous, intravenous, intramuscular, intraperitoneal, transdermal, topical, or buccal routes. Alternatively, or concurrently, administration may be by the oral or nasal route or directly to the lungs. In a preferred embodiment, the compounds of this invention may be administered by inhalation. For inhalation therapy the compound may be in a solution useful for administration by liquid aerosol, metered dose inhalers, or in a form suitable for a dry powder inhaler. The dosage administered will be dependent upon the age, health, and weight of the recipient, kind of concurrent treatment, if any, frequency of treatment, and the nature of the effect desired.

In some preferred embodiments, the agents of the present invention may be formulated as aerosols. The formulation of pharmaceutical aerosols is routine to those skilled in the art, see for example, Sciarra, J. in Remington: The Science and Practice of Pharmacy 19$^{th}$ Edition, Chapter 95, Mack Publishing Company, Easton, Pa. The agents may be formulated as solution aerosols, dispersion or suspension aerosols of dry powders, emulsions or semisolid preparations. The aerosol may be delivered using any propellant system known to those skilled in the art. The aerosols may be applied to the upper respiratory tract, for example by nasal inhalation, or to the lower respiratory tract or to both.

The compounds used in the method of treatment of this invention may be administered systemically or topically, depending on such considerations as the condition to be treated, need for site-specific treatment, quantity of drug to be administered and similar considerations.

Any common topical formation such as a solution, suspension, gel, ointment or salve and the like may be employed. Preparation of such topical formulations are well described in the art of pharmaceutical formulations as exemplified, for example, by Remington's Pharmaceutical Sciences. For topical application, these compounds could also be administered as a powder or spray, particularly in aerosol form. The active ingredient may be administered in pharmaceutical compositions adapted for systemic administration. As is known, if a drug is to be administered systemically, it may be confected as a powder, pill, tablet or the like or as a syrup or elixir for oral administration. For intravenous, intra-peritoneal or intra-lesional administration, the compound will be prepared as a solution or suspension capable of being administered by injection. In certain cases, it may be useful to formulate these compounds in suppository form or as an extended release formulation for deposit under the skin or intramuscular injection.

An effective amount of a composition or agent contained therein is that amount that will reduce, decrease or down-regulate mucin activation, function, stability, or synthesis. Preferred compositions or agents reduce, decrease or down-regulate chloride channel dependent mucin activation, function, stability, or synthesis, including ICACC chloride channel dependent mucin activation, function, stability, or synthesis. A given effective amount will vary from condition to condition and in certain instances may vary with the severity of the condition being treated and the patient's susceptibility to treatment. Accordingly, a given effective amount will be best determined at the time and place through routine experimentation. It is anticipated, however, that in the treatment of chronic obstructive pulmonary disorders in accordance with the present invention, a formulation containing between 0.001 and 5 percent by weight, preferably about 0.01 to 1%, will usually constitute a therapeutically effective amount. When administered systemically, an amount between 0.01 and 100 mg per kg body weight per day, but preferably about 0.1 to 10 mg/kg/day, will effect a therapeutic result in most instances.

When administered via inhalation, an amount between 0.01 and 100 mg per kg body weight per day, but preferably about 0.10 to 10 mg/kg/day, will effect a therapeutic result in most instances. In some instances, a metered dose aerosol unit contains about 0.8 mg of a compound of the present invention, for instance, talniflumate. At this formulation, the maintenance dose for an adult is about 2 inhalations (about 1.6 mg) twice daily (about 3.2 mg).

The invention also includes pharmaceutical compositions comprising the compounds of the invention together with a pharmaceutically acceptable carrier. Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously or by inhalation. Saline or phosphate buffered saline can also be employed as carriers, particularly for inhalation by aerosols. Lactated saline solutions and aqueous dextrose and glycerol solutions can also be employed as liquid carriers, particularly for injectable solutions. Suitable pharmaceutical carriers are described in Remington's Pharmaceutical Sciences, Mack Publishing Company, 1995.

In addition to the pharmacologically active agent, the compositions of the present invention may contain suitable pharmaceutically acceptable carriers comprising excipients and auxiliaries that facilitate processing of the active compounds into preparations that can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers as described above. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof. Suitable formulations for oral inhalation or nasal inhalation include aqueous solutions with or without excipients well known in the art.

Therapeutic or pharmaceutical compositions or formulations of the invention may be packaged in containers, vials, inhalation devices, etc. with instructions or labels addressing the ability of the composition or formulation to promote lower respiratory tract drainage by thinning bronchial secretions, lubricating irritated respiratory tract membranes through increased mucous flow and/or facilitating the decreased production and removal of viscous, inspissated mucus. The label or instruction may also address indications and useage such as the maintenance of symptomatic relief of various conditions as herein described, including but not limited to, moderate to severe asthma, chronic bronchitis, cystic fibrosis, upper and lower respiratory tract infections and other conditions complicated by the persistence of viscous mucus in the respiratory tract or other places in the body.

The devices of the present invention may be any device adapted to introduce one or more therapeutic compositions into the upper and/or lower respiratory tract. In some preferred embodiments, the devices of the present invention may be metered-dose inhalers. The devices may be adapted to deliver the therapeutic compositions of the invention in the form of a finely dispersed mist of liquid, foam or powder. The devices may use any propellant system known to those in the art including, but not limited to, pumps, liquefied-gas, compressed gas and the like. Devices of the present invention typically comprise a container with one or more valves throw which the flow of the therapeutic composition travels and an actuator for controlling the flow. Suitable devices for use in the present invention may be seen in, for example, in Remington: The Science and Practice of Pharmacy, $19^{th}$ Edition, Chapter 95, pages 1676–1692, Mack Publishing Co., Easton, Pa. 1995.

The practice of the present invention may employ the conventional terms and techniques of molecular biology, pharmacology, immunology and biochemistry that are within the ordinary skill of those in the art. For example, see Sambrook et al., Molecular Cloning: A Laboratory Manual, 2nd edition, Cold Spring Harbor Laboratory Press, 1985.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

NFA Inhibits Mucin Production by Caco2 Cells Activated to Over-Produce Mucin

Figure 2:
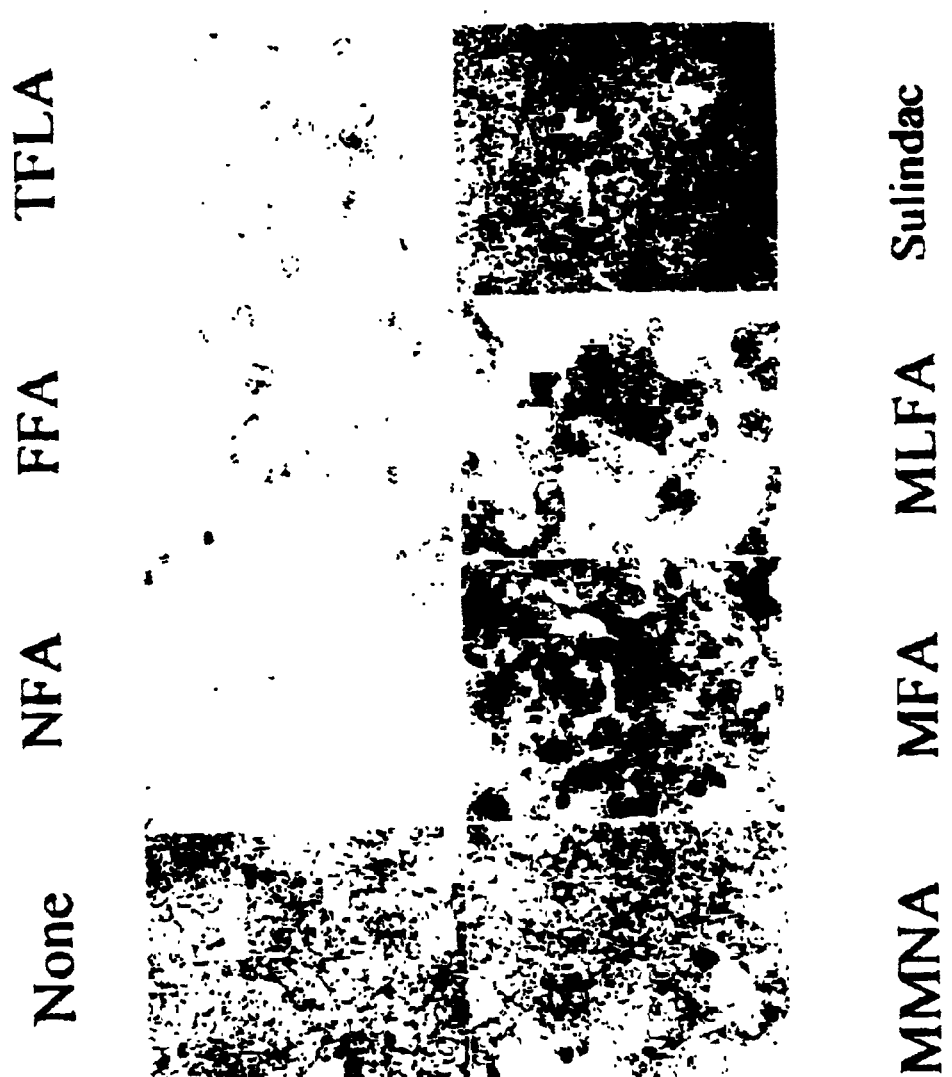
FIG. 2 shows the ability of NFA and various compounds to suppress the over-production of mucin by activated Caco2 cells. This figure shows the inhibition of mucin production in activated Caco2 cells by fenamates.
Figure 3:
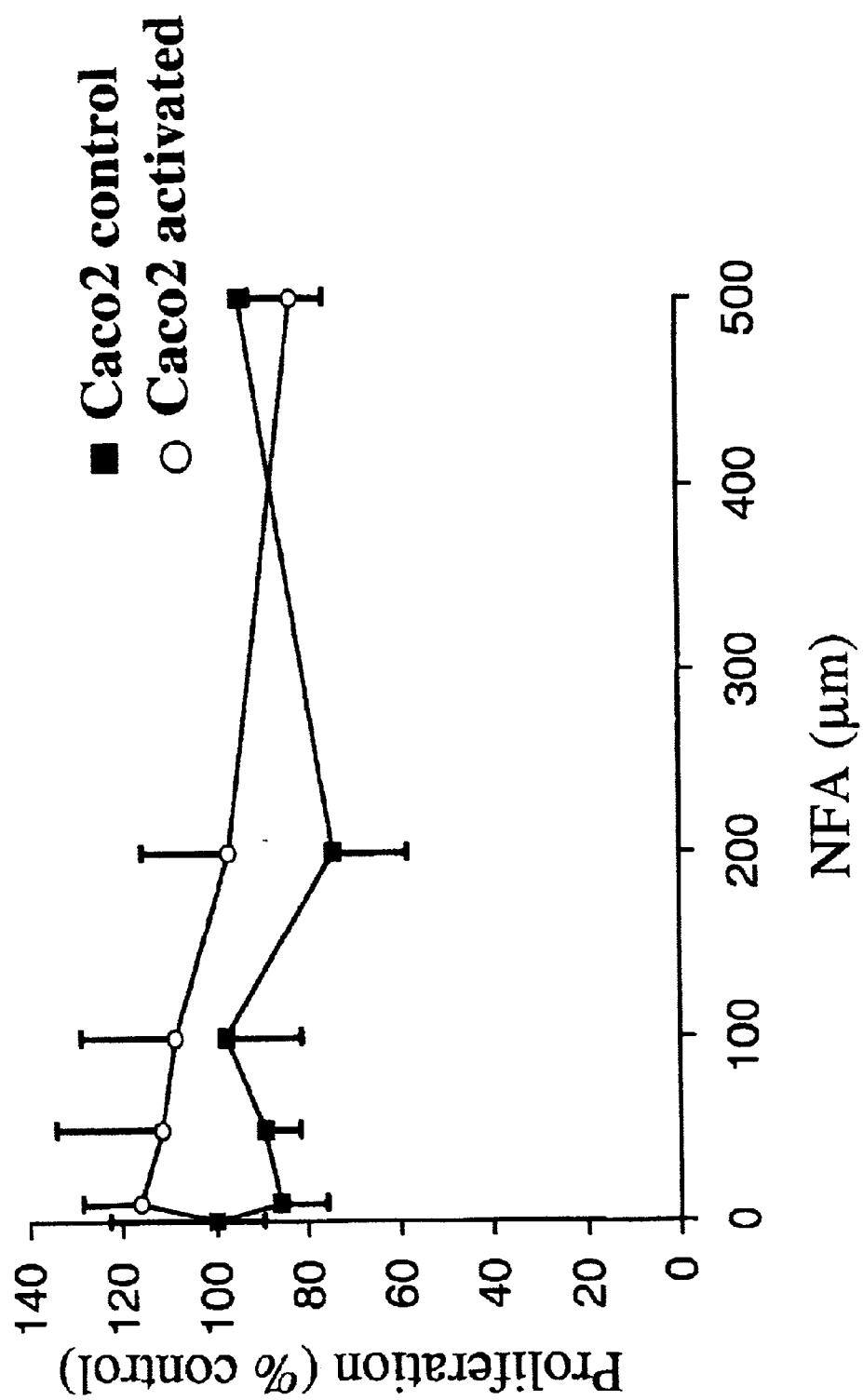
FIG. 3 shows that treatment of the activated Caco2 cell line with NFA did not effect their viability. This figure shows that NFA does not effect epithelial cell proliferation.
Figure 11:
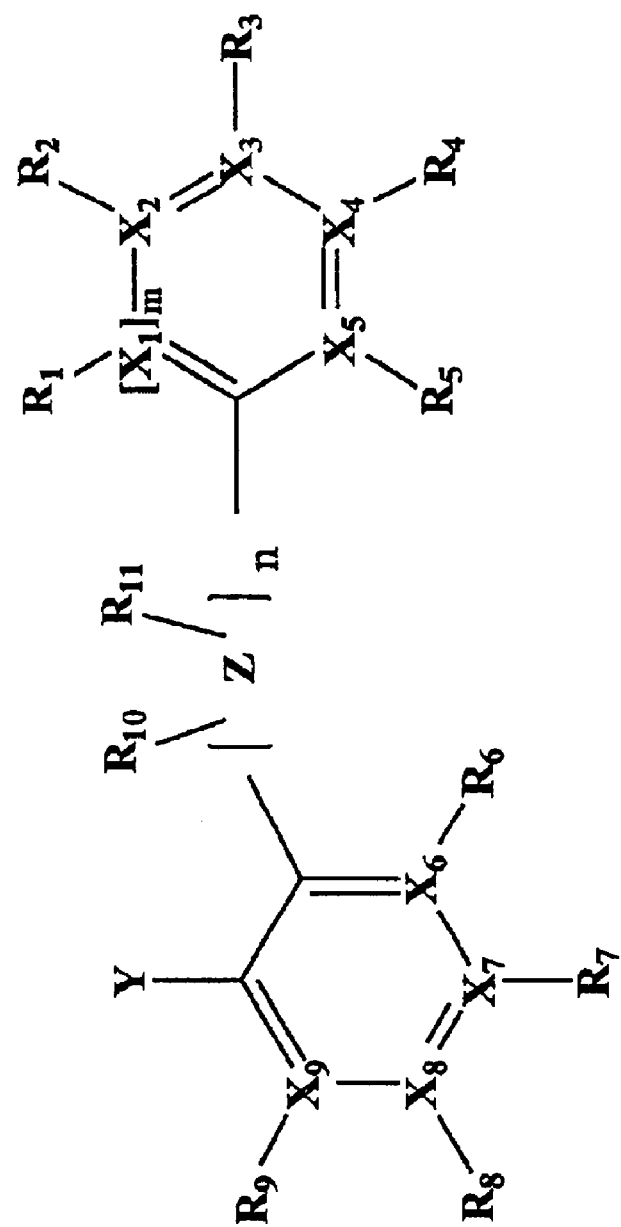
FIG. 11 shows a generic formula for phenyl anthranilic acid analogues that block mucin production wherein $X_1$ to $X_9$=each independently of the others may be C, S, O or N, $R_1$ to $R_{11}$=each independently of the others may be hydrogen, alkyl, aryl, substituted alkyl, substituted aryl, halogen, halogen substituted alkyl, halogen substituted aryl, alkyl or aryl forming a ring, substituted alkyl or aryl forming a ring, hydroxyl, alkyl or aryl ether, amine, alkyl or aryl amine, alkyl or aryl ester, alkyl or aryl sulfonamide, thiol, alkyl or aryl thioether, alkyl or aryl sulfone, alkyl or aryl sulfoxide or sulfonamide, Y=carboxylate, alkyl carboxylate, sulfate, sulfonate, phosphate, phosphonate, amides of carboxylic acids, esters of carboxylic acids, amides of phosphoric acids, esters of phosphoric acids, amides of sulfonic acids, esters of sulfonic acids, amides of phosphonic acids, esters of phosphonic acids, sulfonamide, phosphonamide, tetrazole, hydroxamic acid or other acid isostere, Z=O, $NR_{10}$, S, $CR_{10}R_{11}$, sulfoxide or sulfone, m=0 or 1, n=1 or 2.

Activated Caco2 cells that express the mRNA of MUC1, MUC2, MUC3, MUC4, MUC5B and MUC5AC have been produced and used to test for inhibitors of mucin production. These cells can be stained for mucin using Periodic Acid-Schiff staining (PAS). As shown in FIG. 1, although Caco2 control cells displayed a basal PAS staining with a few small glycoconjugates vesicles scattered about (panel A), activation of the Caco2 cells dramatically increased the number and intensity of PAS positive mucin glycoconjugates (panel B). The activated Caco2 cells were cultured in the presence of niflumic acid (NFA) or 4,4'-diisothiocyanostilbene-2,2'-disulfonic acid (DIDS). At the indicated concentrations (100 $\mu$m for NFA and 300 $\mu$m for DIDS), PAS staining of inhibitor treated activated Caco2 cells revealed significantly fewer positive staining mucin glycoconjugates as compared with the untreated cells (FIG. 1D compared to 1B). In addition, the slight staining seen in control cells was also inhibited (FIG. 1C compared to 1A). Mucin production by activated Caco2 cells could also be inhibited by other fenamates such as Flufenamate (FFA), Tolfenamate (TFLA) and partially by Mefenamate (MFA) and Meclofenamate (MLFA) (FIG. 2). Related compounds Naproxen (MMNA) and Sulindac were ineffective. This reduced mucin production in NFA treated cells was not due to dramatic changes of the physiological condition of the cells, since their viability was not affected by even higher concentrations of NFA (FIG. 3). Taken in total, the results are consistent with these drugs inhibiting epithelial activation. Moreover, the results clearly demonstrate a direct effect of NFA and its analogues (Phenyl anthranilic acid derivatives shown in FIG. 11), DIDS, and SIDS on mucus over-production, which is a hallmark of multiple chronic obstructive pulmonary disorders.

Example 2

NFA Inhibits Eotaxin Production by Caco2 Cells Activated to Over-Produce Mucin

Figure 4:
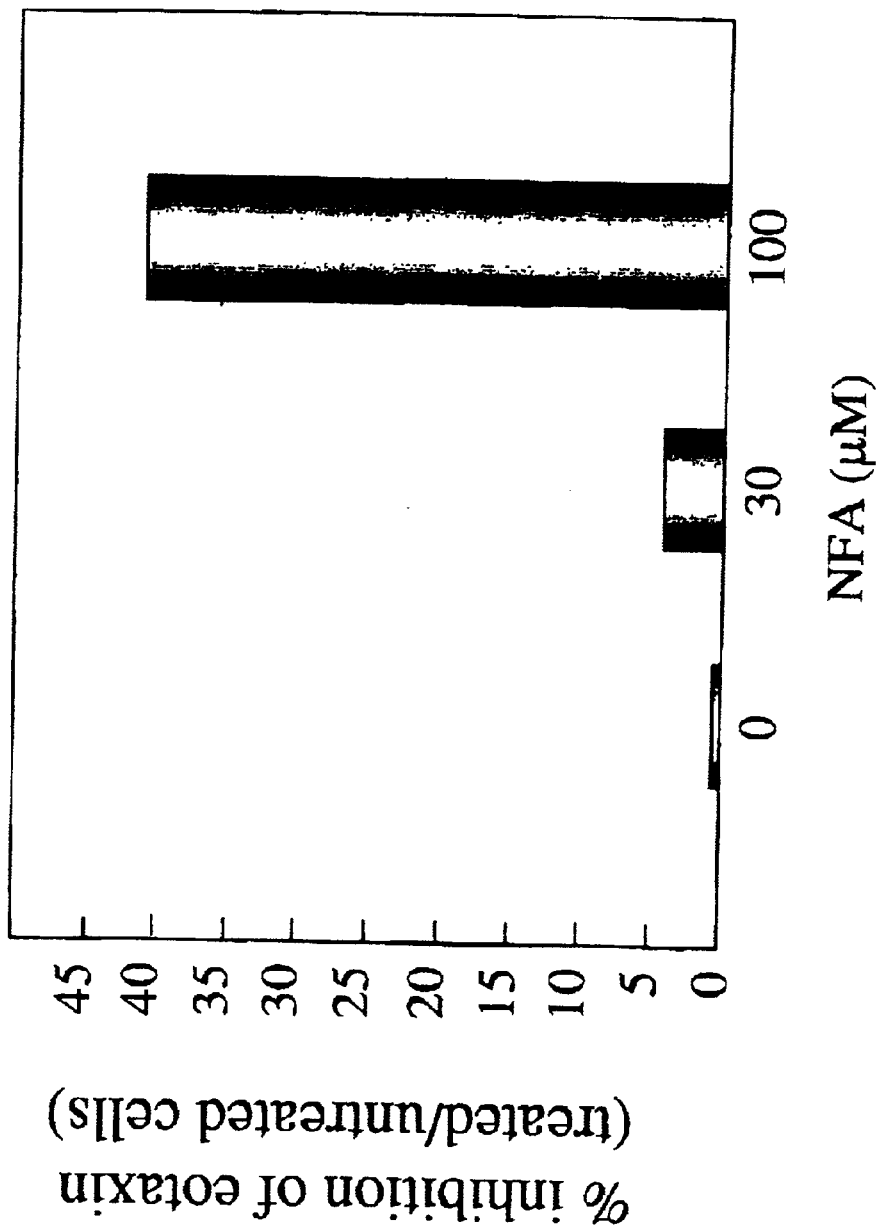
FIG. 4 shows the inhibition of epithelial cell production of the chemokine eotaxin. This figure shows that NFA blocks epithelial activation including chemokine production.

Activated LHL4 cells that express and secrete eotaxin have been produced and used to test for inhibitors of eotaxin production. These cells were assayed in vitro for eotaxin by an ELISA technique well known in the art (R&D Systems). As shown in FIG. 4, activated LHL4 cells were cultured in the absence (control) or presence of increasing concentrations of niflumic acid (NFA). Significant inhibition of eotaxin production was noted with increasing concentrations of NFA. Similar inhibition was seen with DIDS and SIDS in an identical experiment. Mad/C3 cells show similar inhibition of eotaxin production by NFA, DIDS, and SIDS. Taken together, these results clearly demonstrate a direct effect of NFA on eotaxin production.

Example 3

Inhibition of Mucin Overproduction in Murine Models of Asthma by NFA

Certified virus-free male and female mice of the following strains, DBA, C57B6 and B6D2F1 were purchased from the National Cancer Institute or Jackson Laboratories (Bar Harbor Me.). IL-9 transgenic mice (Tg5) and their parent strain (FVB), were obtained from the Ludwig Institute (Brussels, Belgium). Animals were housed in a high-efficiency, particulate filtered air facility and allowed free access to food and water for 3 to 7 days prior to experimental manipulation. The animal facilities were maintained at 22° C. and the light:dark cycle was automatically controlled (10:14 hour light:dark).

Phenotyping and Efficacy of Pretreatment.

Animals either received no pretreatment or were sensitized by nasal aspiration of Aspergillus fumigatus antigen to assess the effect of pretreatment on bronchial hyperresponsiveness, composition of bronchoalveolar lavage fluid, mucin production and serum IgE. Mice were challenged with Aspergillus or saline intranasally (on days 0, 7, 14, 21 and 22) and phenotyped 24 hours after the last dose. Sensitized mice were treated on days 0–21 with either PBS or 100 μg of NFA by intra-tracheal instillation (IT). The inhibition of mucus production and mucin expression in the lung was used to assess the treatment effect of NFA, or could be used to assess the treatment effects of other drug candidates. To determine the bronchoconstrictor response, respiratory system pressure was measured at the trachea and recorded before and during exposure to the drug. Mice were anesthetized and instrumented as previously described. (Levitt et al., 1988; Levitt and Mitzner, 1989; Kleeberger et al., 1990; Levitt, 1991; Levitt and Ewart, 1995; Ewart et al., 1995). Airway responsiveness is measured to one or more of the following: 5-hydroxytryptamine, acetylcholine, atracurium or a substance-P analog. A simple and repeatable measure of the change in peak inspiratory pressure following bronchoconstrictor challenge was used which has been termed the Airway Pressure Time Index (APTI) (Levitt et al., 1988; Levitt and Mitzner, 1989). The APTI was assessed by the change in peak respiratory pressure integrated from the time of injection until the peak pressure returns to baseline or plateau. The APTI was comparable to airway resistance, however, the APTI includes an additional component related to the recovery from bronchoconstriction.

Prior to sacrifice, whole blood was collected for serum IgE measurements by needle puncture of the inferior vena cava in anesthetized animals. Samples were centrifuged to separate cells and serum was collected and used to measure total IgE levels. Samples not measured immediately were frozen at −20° C.

All IgE serum samples were measured using an ELISA antibody-sandwich assay. Microtiter plates were coated, 50 μl per well, with rat anti-murine IgE antibody (Southern Biotechnology) at a concentration of 2.5 μg/ml in a coating buffer of sodium carbonate-sodium bicarbonate with sodium azide. Plates were covered with plastic wrap and incubated at 4° C. for 16 hours. The plates were washed three times with a wash buffer of 0.05% Tween-20 in phosphate-buffered saline, incubating for five minutes for each wash. Blocking of nonspecific binding sites was accomplished by adding 200 μl per well 5% bovine serum albumin in phosphate-buffered saline, covering with plastic wrap and incubating for 2 hours at 37° C. After washing three times with wash buffer, duplicate 50 μl test samples were added to each well. Test samples were assayed after being diluted 1:10, 1:50 and 1:100 with 5% bovine serum albumin in wash buffer. In addition to the test samples, a set of IgE standards (PharMingen) at concentrations from 0.8 ng/ml to 200 ng/ml in 5% bovine serum albumin in wash buffer, were assayed to generate a standard curve. A blank of no sample or standard was used-to zero the plate reader (background). After adding samples and standards, the plate was covered with plastic wrap and incubated for 2 hours at room temperature. After washing three times with wash buffer, 50 μl of secondary antibody rat anti-murine IgE-horseradish peroxidase conjugate was added at a concentration of 250 ng/ml in 5% bovine serum albumin in wash buffer. The plate was covered with plastic wrap and incubated 2 hours at room temperature. After washing three times with wash buffer, 100 μl of the substrate 0.5 mg/ml o-phenylenediamine in 0.1 M citrate buffer was added to every well. After 5–10 minutes the reaction was stopped with 50 μl of 12.5% sulfuric acid and absorbance was measured at 490 nm on a MR5000 plate reader (Dynatech). A standard curve was constructed from the standard IgE concentrations with antigen concentration on the x axis (log scale) and absorbance on the y axis (linear scale). The concentration of IgE in the samples was interpolated from the standard curve.

Bronchoalveolar lavage (BAL) and cellular analysis were preformed as previously described (Kleeberger et al., 1990). Lung histology was carried out after either the lungs were filled with fixative in situ and place in formalin, or extracted and immediately frozen in liquid nitrogen. Since prior instrumentation may introduce artifact, separate animals were used for these studies. Thus, a small group of animals was treated in parallel exactly the same as the cohort undergoing various pre-treatments except these animals were not used for other tests aside from bronchial responsiveness testing. After bronchial responsiveness testing, lungs were removed and submersed in liquid nitrogen as above. Cryosectioning, staining, and histologic examination was carried out in a manner obvious to those skilled in the art.

Figure 5:
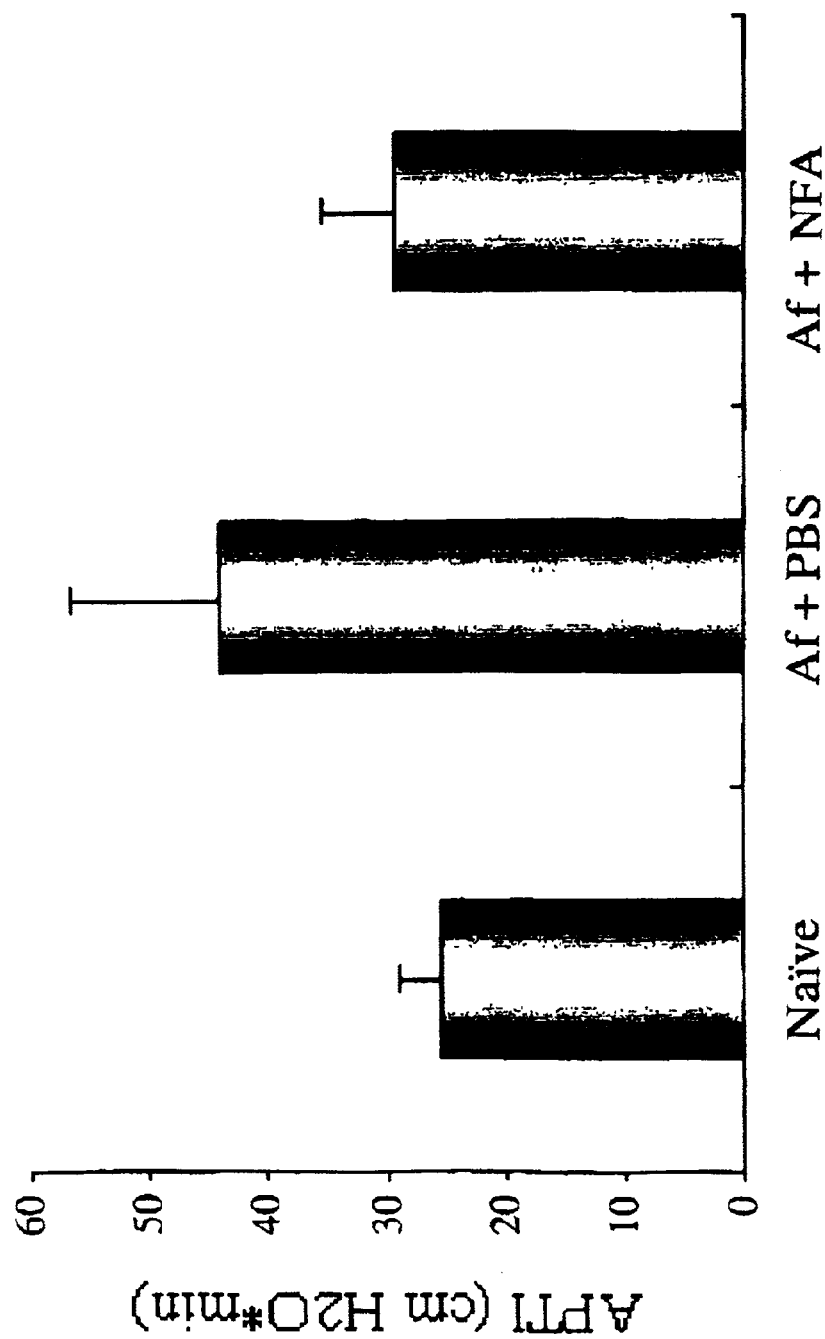
FIG. 5 shows that intra-tracheal administration of NFA suppresses antigen-induced airway hyperresponsiveness (Af+NFA) compared to phosphate buffered saline (PBS). This figure shows that NFA blocks epithelial antigen responses including airway hyperresponsiveness.
Figure 6:
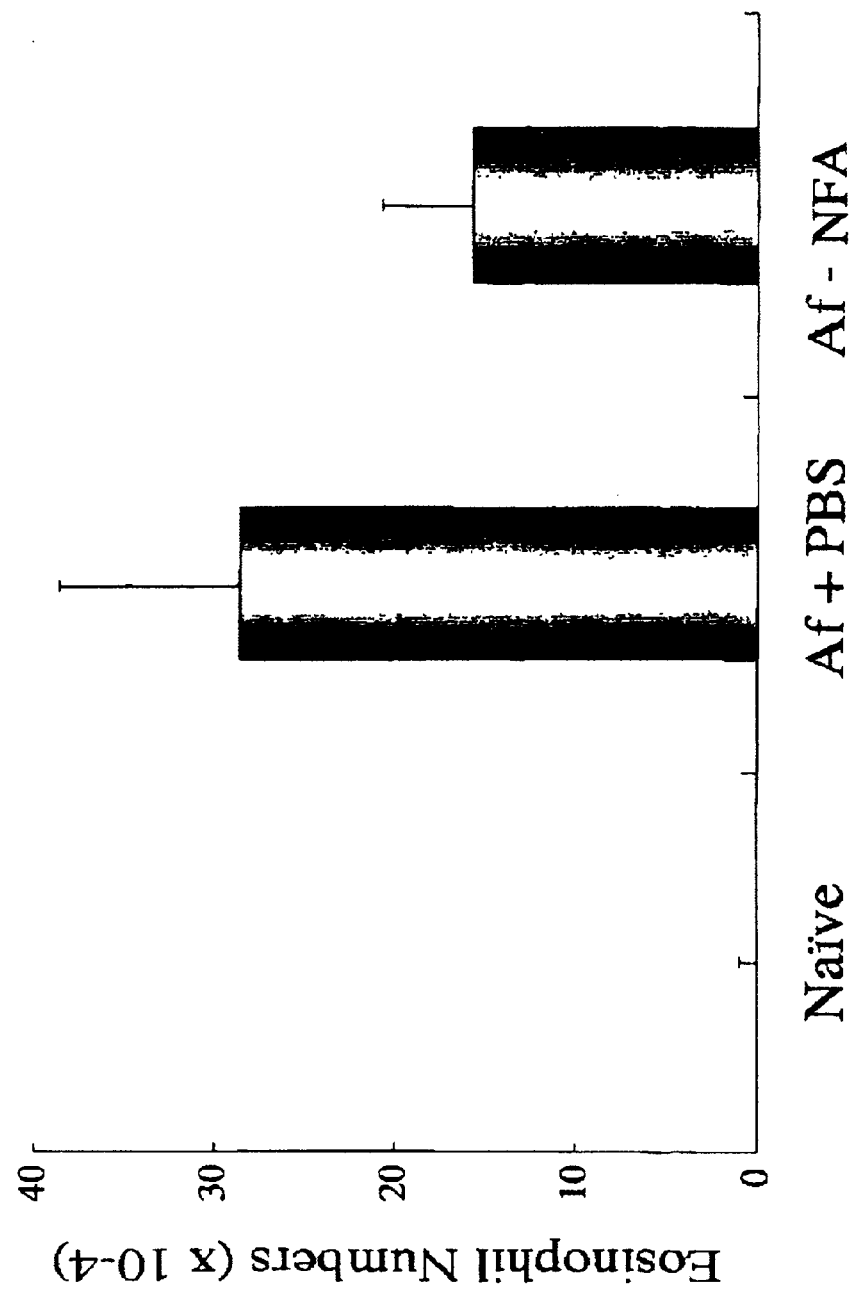
FIG. 6 shows the results of intra-tracheal administration of NFA. This figure shows that NFA reduces antigen-induced lung eosinophilia in vivo. This is seen by comparing eosinophilia after activation with Aspergillus in the presence of NFA (Af+NFA) to eosinophilia after activation in the absence of NFA phosphate buffered saline (Af+PBS).
Figure 7:
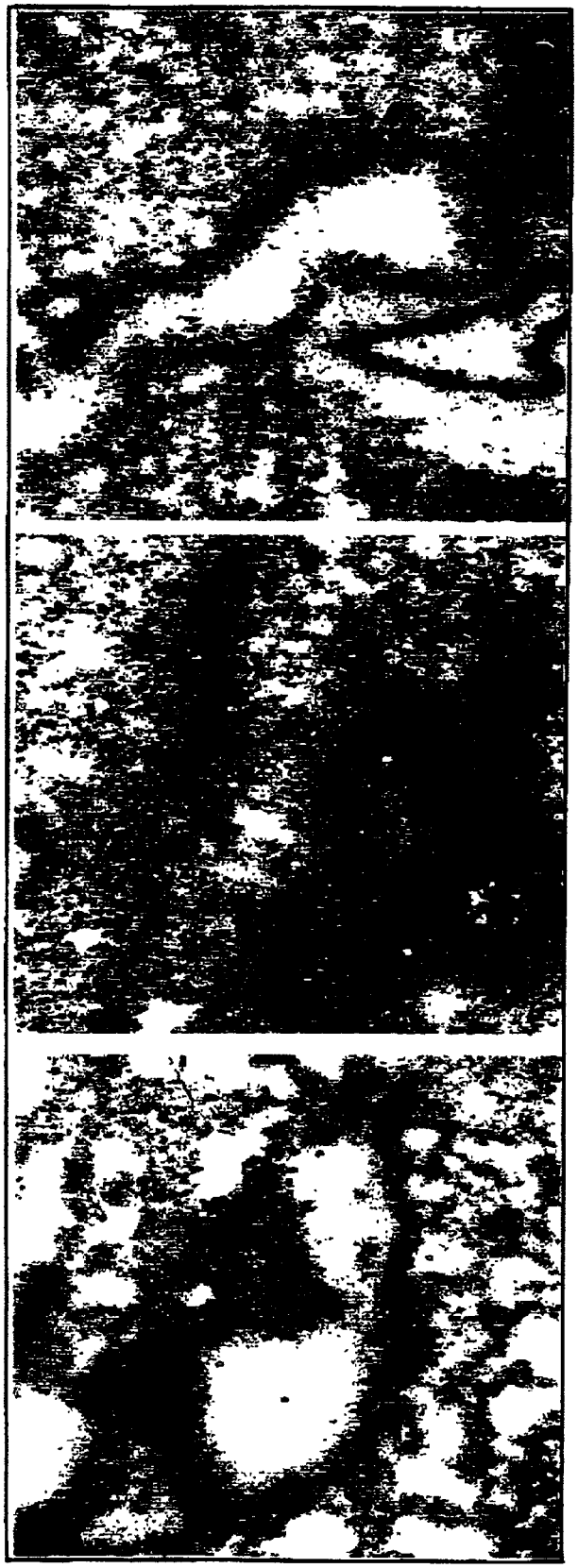
FIG. 7 shows the results of intra-tracheal administration of NFA on antigen-induced increases in mucus (mucin glyco-conjugates) (Af+NFA) compared to phosphate buffered saline (PBS). This figure shows NFA blocks increased mucin expression due to antigen in the lungs of exposed mouse.

NFA, which blocks epithelial cell activation and down-regulates mucin and eotaxin production in vitro, was used therapeutically to assess the importance of epithelial cell activation in vivo on antigen-induced mucin production, bronchial responsiveness, serum IgE, and airway inflammation as assessed by BAL in mice. The effects of NFA treatment, on airway responsiveness, BAL, mucus production, and serum IgE levels relative to vehicle treated matched controls were determined. FIGS. 5 and 6 show that NFA is able to suppress airway hyperresponsiveness and BAL lung eosinophilia respectively, however, there was no effect on serum IgE levels. In addition NFA could also suppress the over-production of mucus in the lung caused by exposure to antigen (FIG. 7).

Example 4

Epithelial Activation by IL9 in a Transgenic Mouse Produces Mucus Over-Production and Mucin Gene Up-Regulation. A Model for Drug Screening Certified virus-free male and female IL9 transgenic mice (IL9TG5-FVB/N) 5–6 weeks of age were bred in our laboratories. Male and female FVB/N mice 5–6 weeks of age were purchased from Jackson Laboratories (Bar Harbor Me.). Animals were housed in high-efficiency, particulate filtered air and allowed free access to food and water for 3 to 7 days prior to experimental manipulation. The animal facilities were maintained at 22° C. and the light:dark cycle was automatically controlled (10:14 hour light:dark).

Phenotyping and Efficacy of Treatment.

Figure 8:
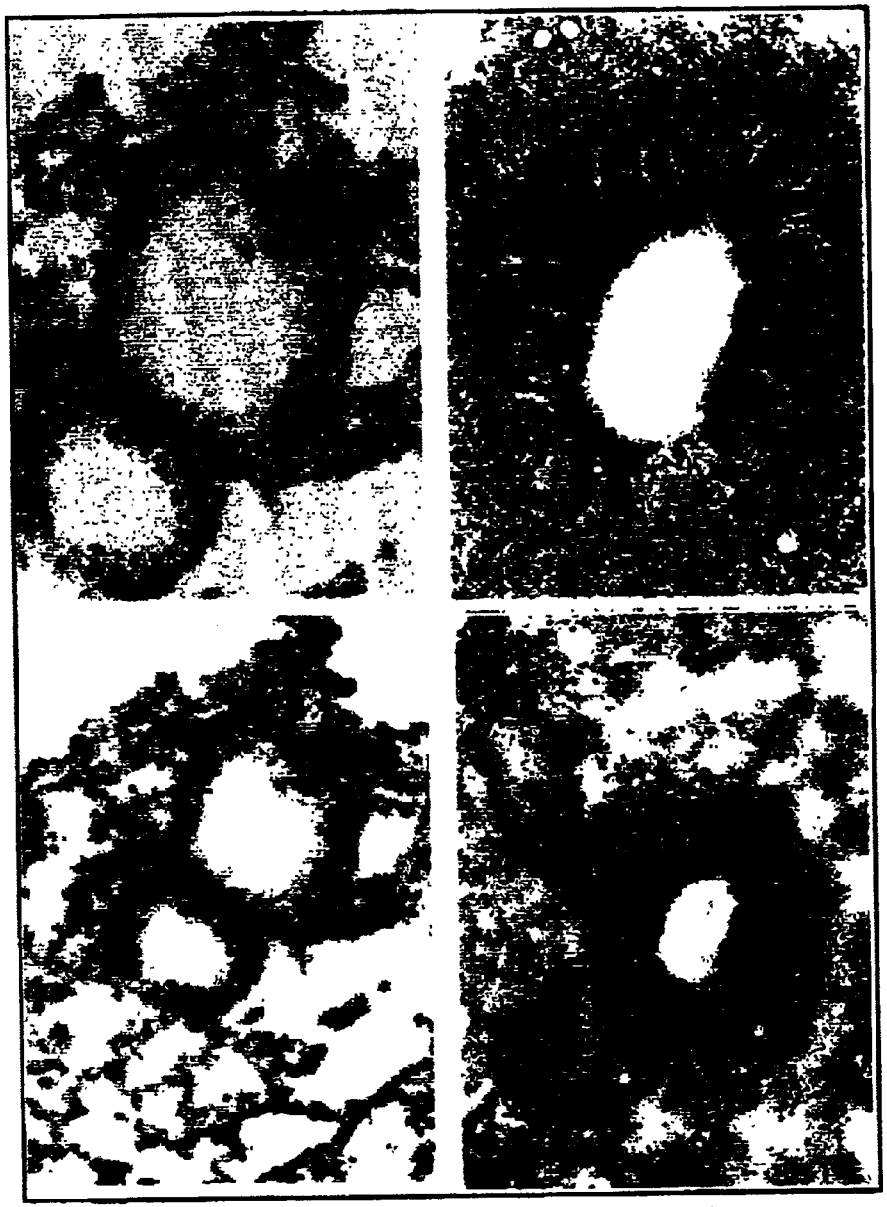
FIG. 8 shows that IL9 transgenic mice constitutively over-produce mucin in the airway in contrast to control FVB mice.
Figure 9:
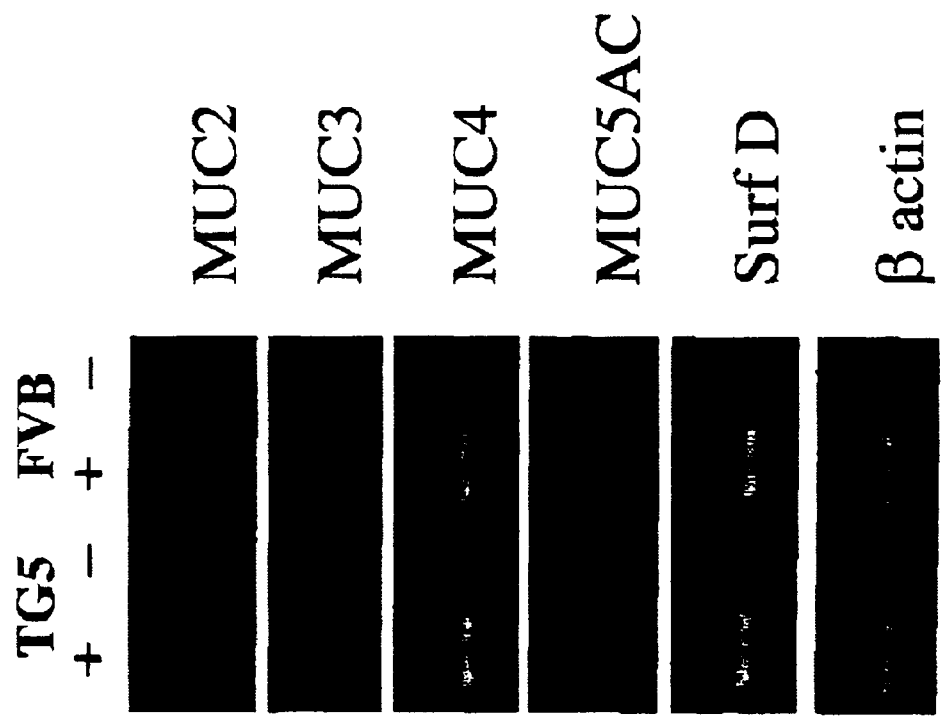
FIG. 9 shows the constitutive over-production of mucin in the lung of IL9 transgenic mice is associated with the specific up-regulation of MUC2 and MUC5AC steady-state transcripts compared to the background strain (FVB/NJ) of mice. This figure shows that specific mucin genes are up-regulated in the lungs of IL-9 transgenic mice.

Animals were phenotyped, naive, or 24 hrs after receiving intra-tracheal (IT) shame (vehicle) treatment, or drugs in the same vehicle as was used in identically treated controls. Mice were treated IT once daily for three days. NFA (100 µg) or antibody to IL-9 were administered in PBS IT. Treatment responses were measured by the assessment of mucin inhibition by histologic exam (PAS staining of greater than 10 sections through the treated and control lungs or western blots of MUC1, MUC2 and MUC3 expression from the same lungs. FIG. 8 shows that IL-9 transgenic mice constitutively overproduce mucin as compared to control FVB mice. A decrease from the high levels of constitutive mucin production that occurs in the asthmatic IL9 transgenic (FIG. 8) (naive and vehicle control) to levels comparable to the much lower baseline mucin production found in the FVB/N lungs (normal positive control) was considered significant for any drug. The up-regulation of mucus production in the IL9 transgenic is specifically associated with increased steady-state mRNA levels of MUC2 and MUC5AC as shown by RT-PCR (FIG. 9).

Neutralizing IL-9 antibody was shown to produce a significant decrease in mucin production in the IL9 transgenic lungs (FIG. 10). NFA also decreased mucin production in this model.

Example 5

Inhibition of Mucin Over Production in Murine Models of Asthma by Talniflumate

Certified virus-free male B6D2F1 mice 5–6 weeks of age were purchased from Jackson Laboratories (Bar Harbor Me.). Animals were housed in high-efficiency, particulate filtered air and allowed free access to food and water 5 to 7 days prior to experimental manipulation. The animal facilities were maintained at 22° C. and the light:dark cycle was automatically controlled (12:12 hour light:dark).

Phenotyping and Efficacy of Treatment.

Animals were fed ad lib either Talniflumate containing mouse chow or regular mouse chow. Animals either received no sensitization or were sensitized by nasal aspiration of Aspergillus fumigatus antigen to assess the effect of pretreatment on bronchial hyperresponsiveness, composition of bronchoalveolar lavage fluid, mucin production and serum IgE. Mice were challenged with Aspergillus intranasally (on days 0, 7, 16 and 17) and phenotyped 24 hours after the last dose. The inhibition of mucus production in the lung was used to assess the treatment effect of Talniflumate, or could be used to assess the treatment effects of other drug candidates. To determine the bronchoconstrictor response, respiratory system pressure was measured at the trachea and recorded before and during exposure to the drug. Mice were anesthetized and instrumented as previously described. (Levitt et al., 1988; Levitt and Mitzner, 1989; Kleeberger et al., 1990; Levitt, 1991; Levitt and Ewart, 1995; Ewart et al., 1995). Airway responsiveness is measured to one or more of the following: 5-hydroxytryptamine, acetylcholine, atracurium or a substance-P analog. A simple and repeatable measure of the change in peak inspiratory pressure following bronchoconstrictor challenge was used which has been termed the Airway Pressure Time Index (APTI) (Levitt et al., 1988; Levitt and Mitzner, 1989). The APTI was assessed by the change in peak respiratory pressure integrated from the time of injection until the peak pressure returns to baseline or plateau. The APTI was comparable to airway resistance, however, the APTI includes an additional component related to the recovery from bronchoconstriction. Bronchoalveolar lavage (BAL) and cellular analysis were preformed as previously described (Kleeberger et al., 1990). Lung histology was carried out after the lungs were harvested and immediately frozen in liquid nitrogen. After bronchial responsiveness testing, lungs were removed and submersed in liquid nitrogen as above. Cryosectioning, staining, and histologic examination was carried out in a manner obvious to those skilled in the art.

Treatment responses were measured by the assessment of mucin inhibition by histologic exam (PAS staining of the treated and control lungs).

Figure 15A:
FIGS. 15A & B show the inhibition of mucin over production by oral administration if Talniflumate in mice.
Figure 15B:
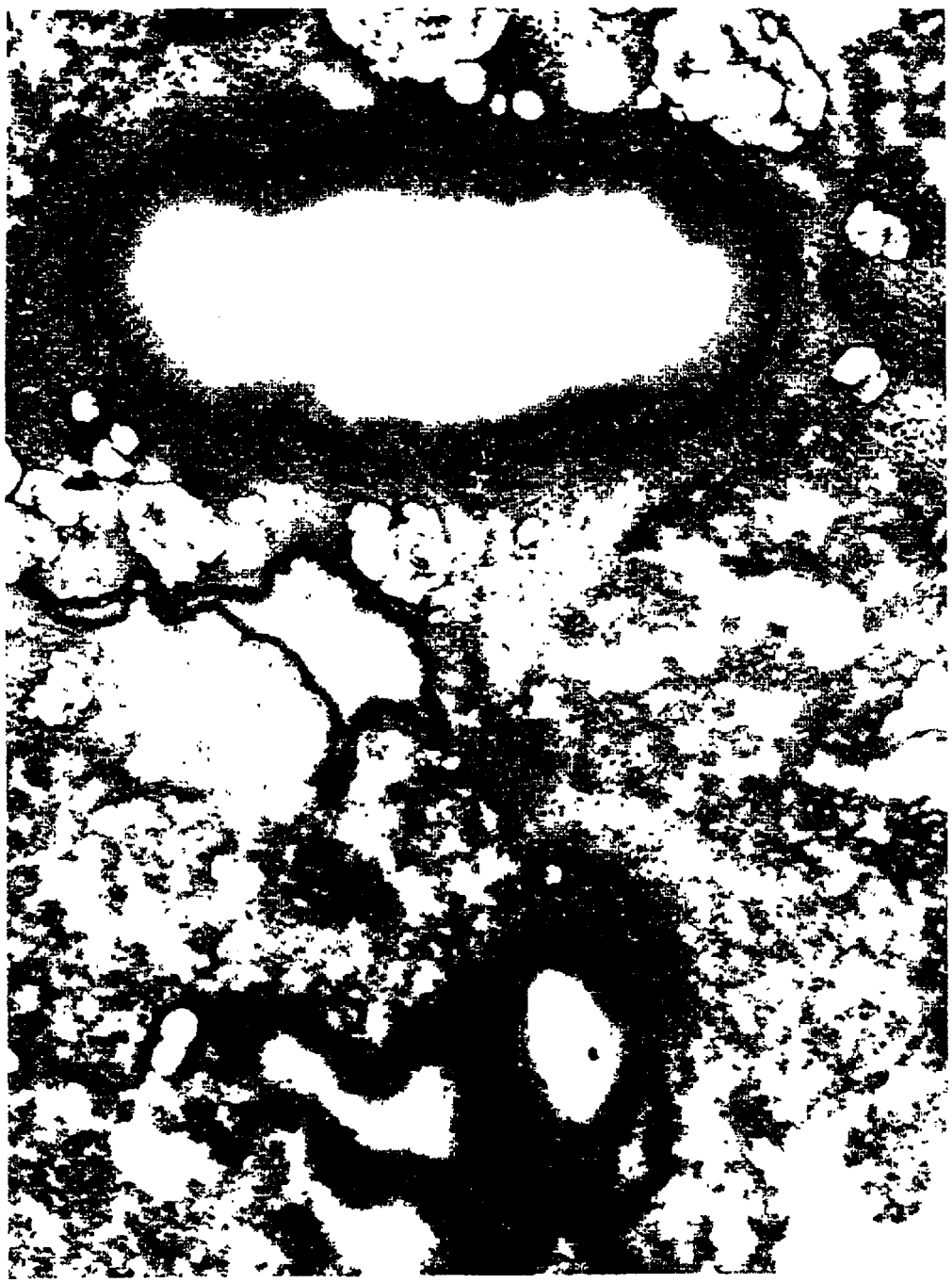
FIG. 15B shows a section of lung (stained with H&E) from a mouse sensitized with *Aspergillus fumigatus* and allowed access to Talniflumate-containing mouse chow.
Figure 16:
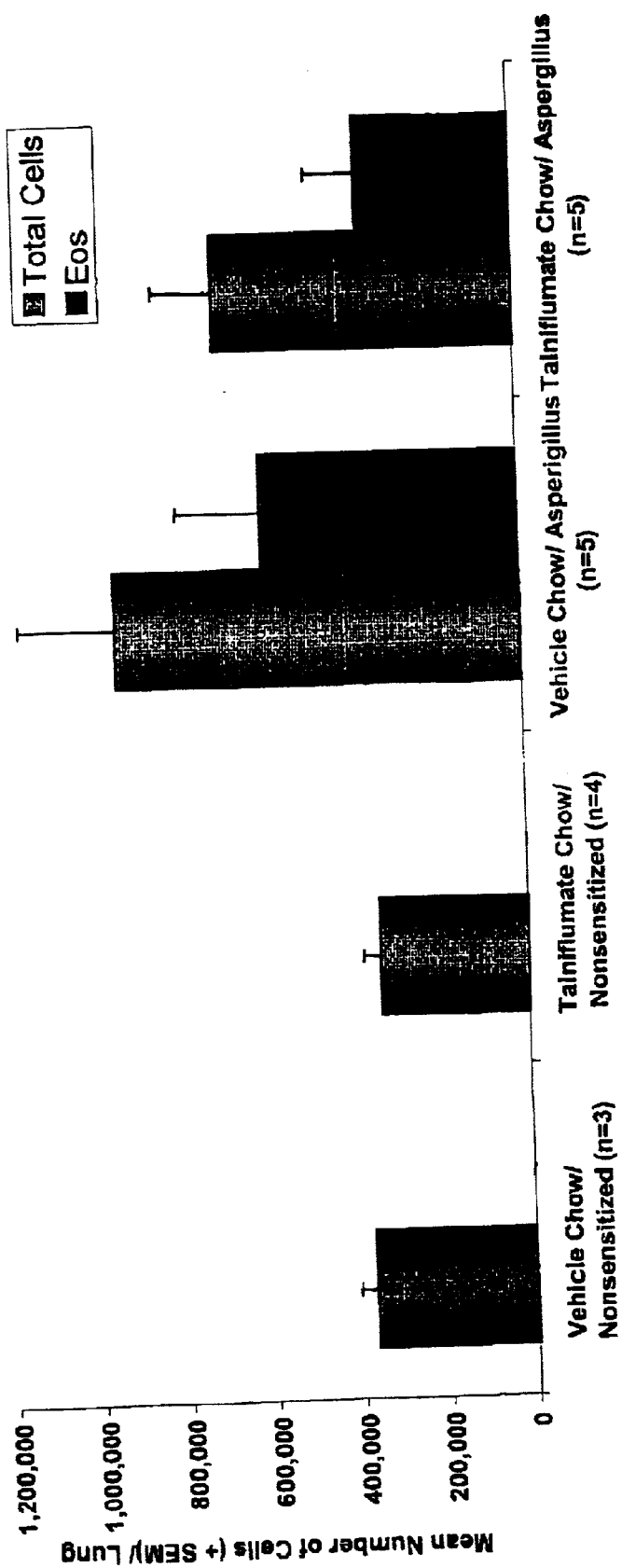
FIG. 16 shows the inhibition of lung eosinophilia by oral administration if Talniflumate in mice. This figure shows AHR373: the effect of Talniflumate mouse chow on BAL of B6D2F1/J male mice sensitized with *Aspergillus fumigatus*.

Oral treatment with Talniflumate reduced mucin staining. FIG. 15A shows the PAS staining in mouse lung obtained from Asp-sens mice that were fed regular mouse chow. FIG. 15B shows the results obtained from Asp-sens mice fed Talniflumate containing chow. FIG. 16 shows the results of feeding talniflumate coated mouse chow on lung eosinophilia determined by bronchoalveolar lavage. Talniflumate reduced the number of eosinophilic cells obtained from mice sensitized to Aspergillus fumigatus as compared to sensitized mice fed standard mouse chow.

Example 6

Overexpression of ICACC-1 in Epithelium Cell Lines Enhances Mucin Production

NCI-H292 cells, a human pulmonary mucoepidermoid carcinoma cell line, were purchased from the American Type Culture Collection (Manassas Va.) and cultured in RPMI1640 medium supplemented with 10% FBS and 1% penicillin/streptomycin (Gibco/BRL). The cells were grown in a humidified, air-containing incubator, supplemented with 5% $CO_2$ at 37° C. Stable NCI-H292 cell lines overexpressing hICACC-1 were established by transfection of pcDNA3-hICACC-1 using a Fujin Transfection kit according to the manufacture's instruction (Boehringer-Mannheim). A control cell line was produced, NCI-H292/ctl, by the transfection of pcDNA3 (ctl) into the NCI-H292 cell line using the same procedure. Expression of the hICACC-1 gene was confirmed for the pcDNA3-hICACC-1 transfectent by Northern analysis.

For s-ELLA (specific enzyme linked lectin assay), cells were plated in 24-well tissue culture plates and incubated for 72 hours to confluence. Supernatants were transferred into 96-well plates pre-coated with 1 µg/ml anti-MUC5A/C antibody (New marker, Fremont Calif.) and blocked with 1% BSA. Antibody bound MUC5A/C was then detected with HRP-lectin (Sigma).

For RT-PCR total RNA was isolated from cell lines using Trizol reagent (Gibco/BRL) following the manufacturer's protocol. RT-PCR was performed by reverse transcribing 1 µg of total RNA and amplifying cDNA with the appropriate primers by PCR. Products were separated by electrophoreses on 2% agarose gels and visualized by ethidium bromide staining. Primer pairs used to generate human ICACC-1 message were: sense 5'-GGCACAGATCTTTTCATTGCTA-3' and antisense 5'-GTGAATGCCAGGAATGGTGCT-3' which produce a 182 bp product. Primer pairs used to generate mucin messages are listed in Table 1.

TABLE 1

(Numbers in parentheses refer to oligonucleotide position contained within the published cDNA).

| Gene (Accession #) | Sense primer (5'-3') | Reverse primer (5'-3') |
|---|---|---|
| HMUC 1 (J05582) | GCCAGTAGCACTCACCATAGCTCG (3113–3136) | CTGACAGACAGCCAAGGCAATGAG (3627–3605) |
| HMUC5AC (AF015521) | GTGGAACCACGATGACAGC (610–629) | TCAGCACATAGCTGCAGTCG (1428–1408) |
| HPMS2 (U13696) | GGACGAGAAGTATAACTTCGAG (2133–2154) | CATCTCGCTTGTGTTAAGAGC (2505–2485) |

Figure 12:
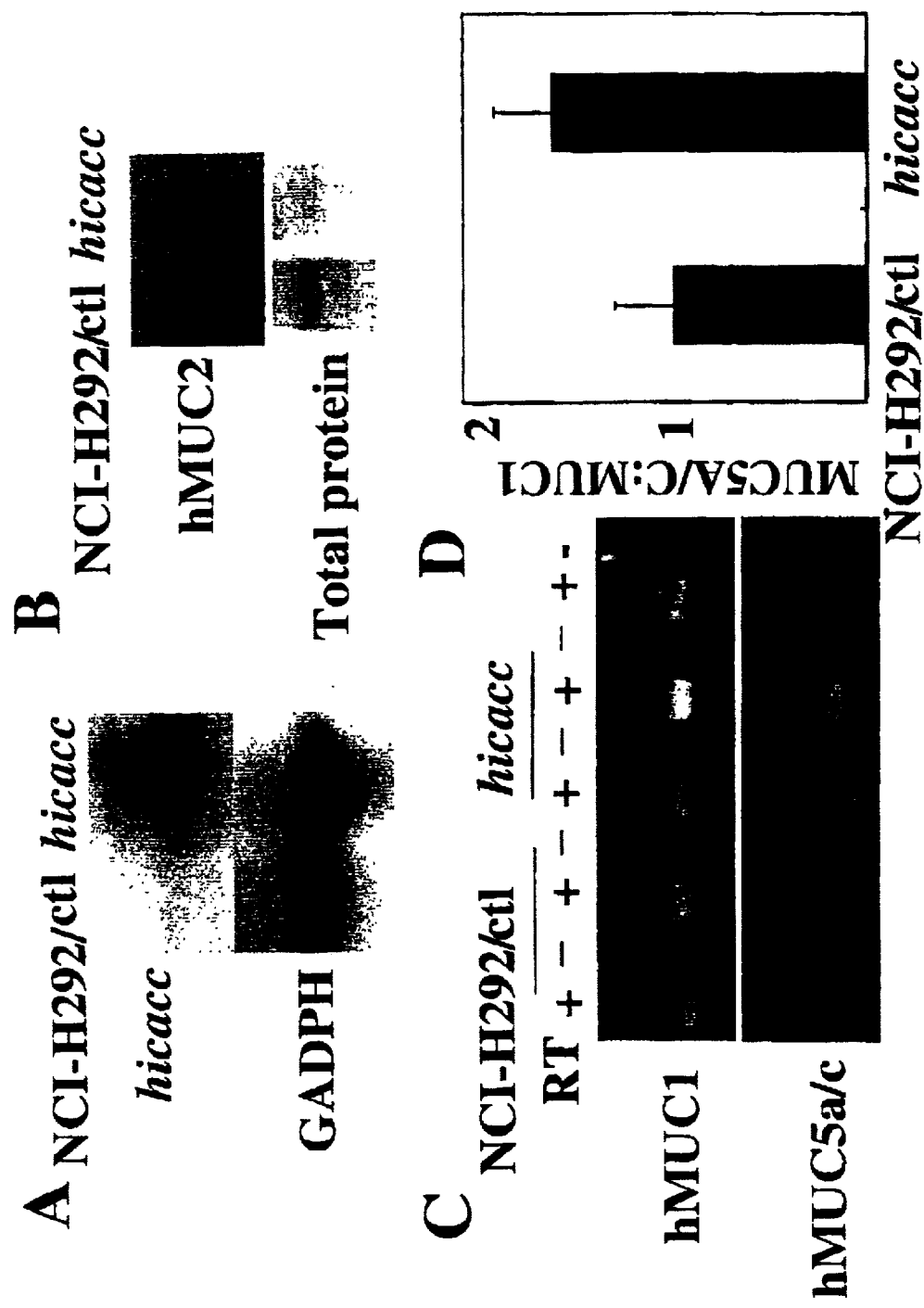
FIG. 12 shows mucin expression induced by hICACC-1 in NCI-H292 cells.

NCI-H292 cells express MUC1 constitutively, whereas MUC2 and MUC5A/C mRNA expression are below detection levels at baseline. FIG. 12A shows the results of a Northern blot analysis of pcDNA3-hICACC-1 transfected cells showing an increased expression level for ICACC mRNA. Western blot analysis of whole cell lysate from ICACC-1 over-expressing clones revealed enhanced MUC2 protein production (FIG. 12B). MUC5A/C expression was significantly increased in ICACC-1 over-expressing cells, while MUC1 was unchanged in RT-PCR analyses (FIG. 12C). Specific ELLA analysis also revealed the overproduction of MUC5A/C protein in ICACC-1 expressing clones compared with the untransfected NCI-H292 cells or cells transfected with empty vector (FIG. 12D).

Example 7

Inhibition of Mucus Over-Production and MUC 5A/C Expression in NCI-H292 Cells Over-Expressing hICACC-1

Figure 13:
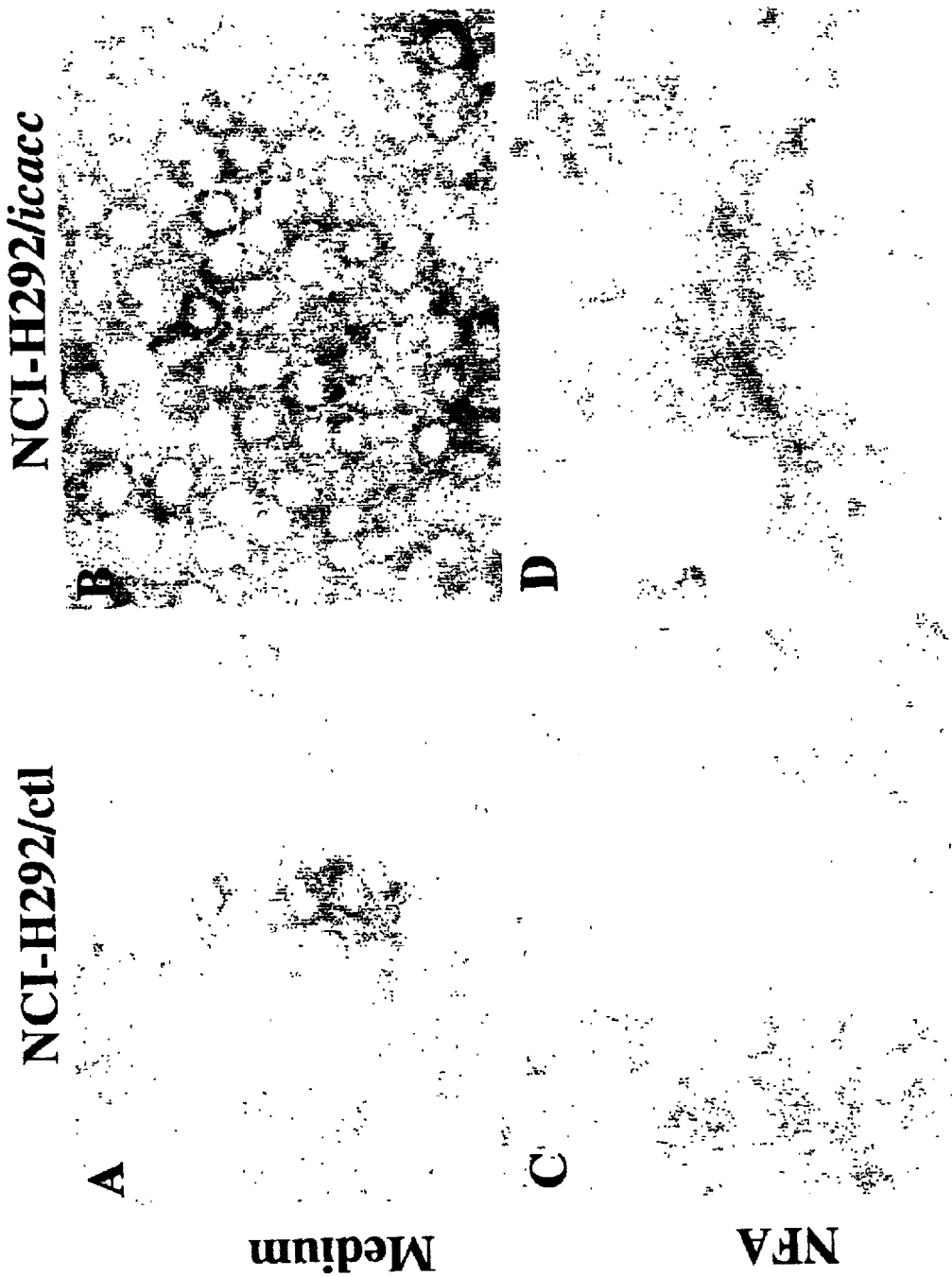
FIG. 13 shows mucus over-production in NCI-H292 cells over-expressing hICACC-1.
Figure 14:
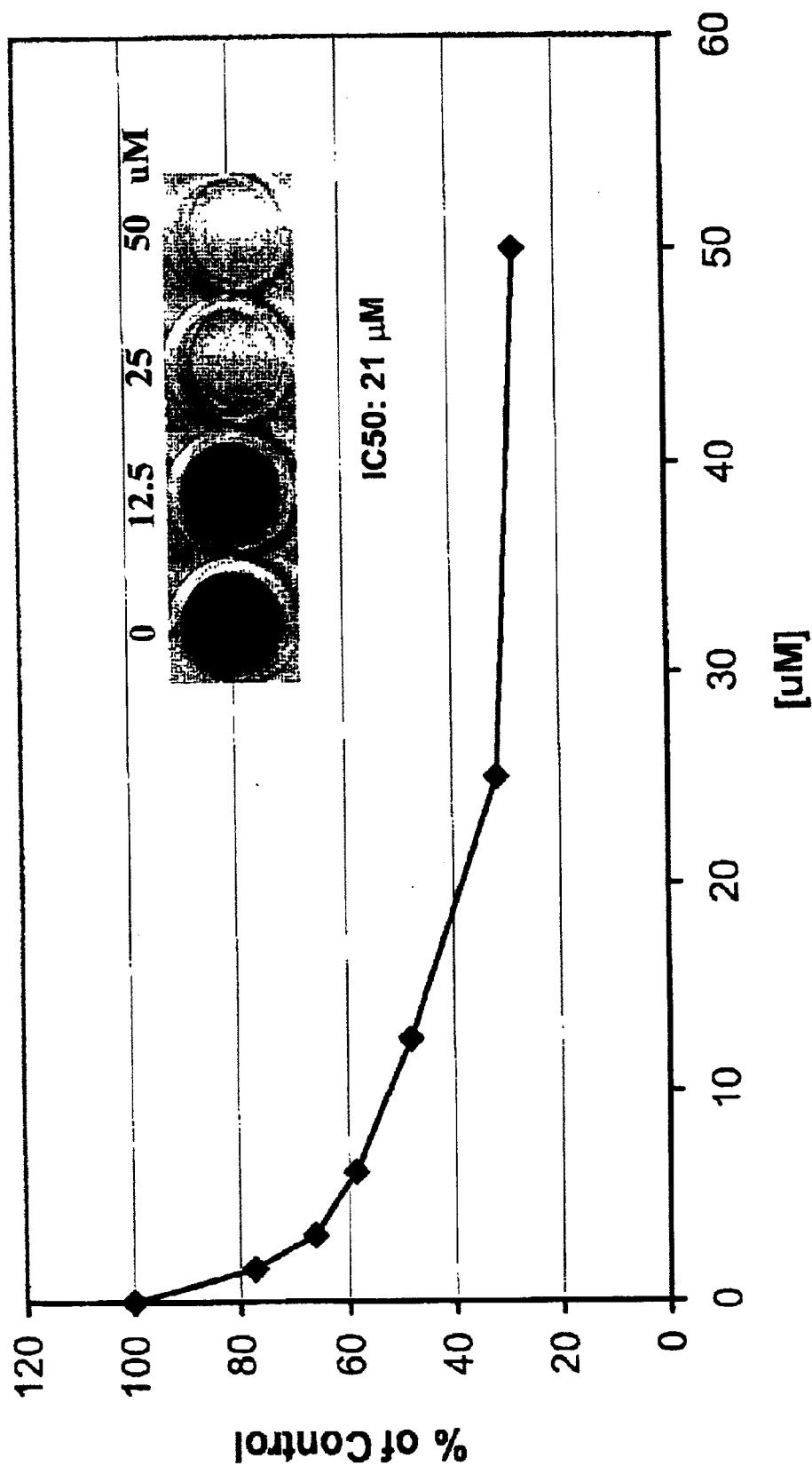
FIG. 14 shows the inhibition of mucin production by Talniflumate.

For the determination of mucous glycoconjugate production, NCI-H292/ctl and NCI-H292/hICACC-1 (AAF 15) cells were cultured in 24-well plates for 3 days. Cells were then fixed with Formalin and mucous glycoconjugates were visualized by AB/PAS staining (Sigma). Although NCI-H292 control cells displayed a basal PAS staining with a few scattered granules (FIG. 13A), over-expression of ICACC-1 dramatically increased the number and intensity of PAS positive muco-glycoconjugates (FIG. 13B). For chloride channel blockage studies, cells were cultured in the presence of niflumic acid (NFA) (Sigma) at 100 $\mu$M concentration, mefanamic acid (MFA) at 125 or 250 $\mu$M or talniflumate at 12.5, 25 or 50 $\mu$M, or media alone. PAS staining of cells treated with NFA, MFA or talniflumate revealed significantly fewer positive staining mucoglycoconjugates compared with untreated cells (FIGS. 13C & D and insert of FIG. 14). PAS staining of inhibitor treated control cells showed virtually no difference from untreated cells (FIGS. 13A & C).

Figure 17:
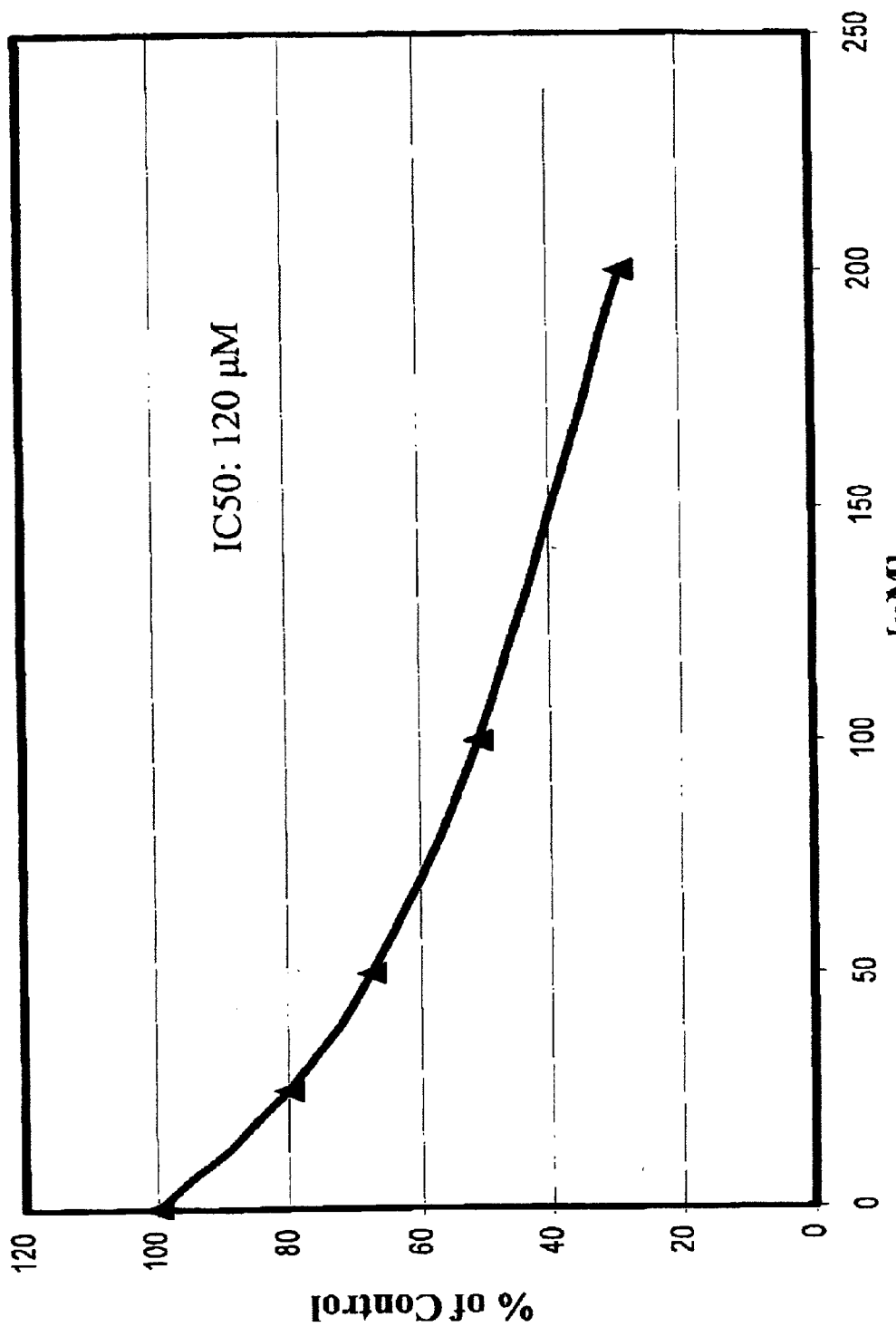
FIG. 17 shows the inhibition of MUC5A/C secretion by Nimesulide.
Figure 18:
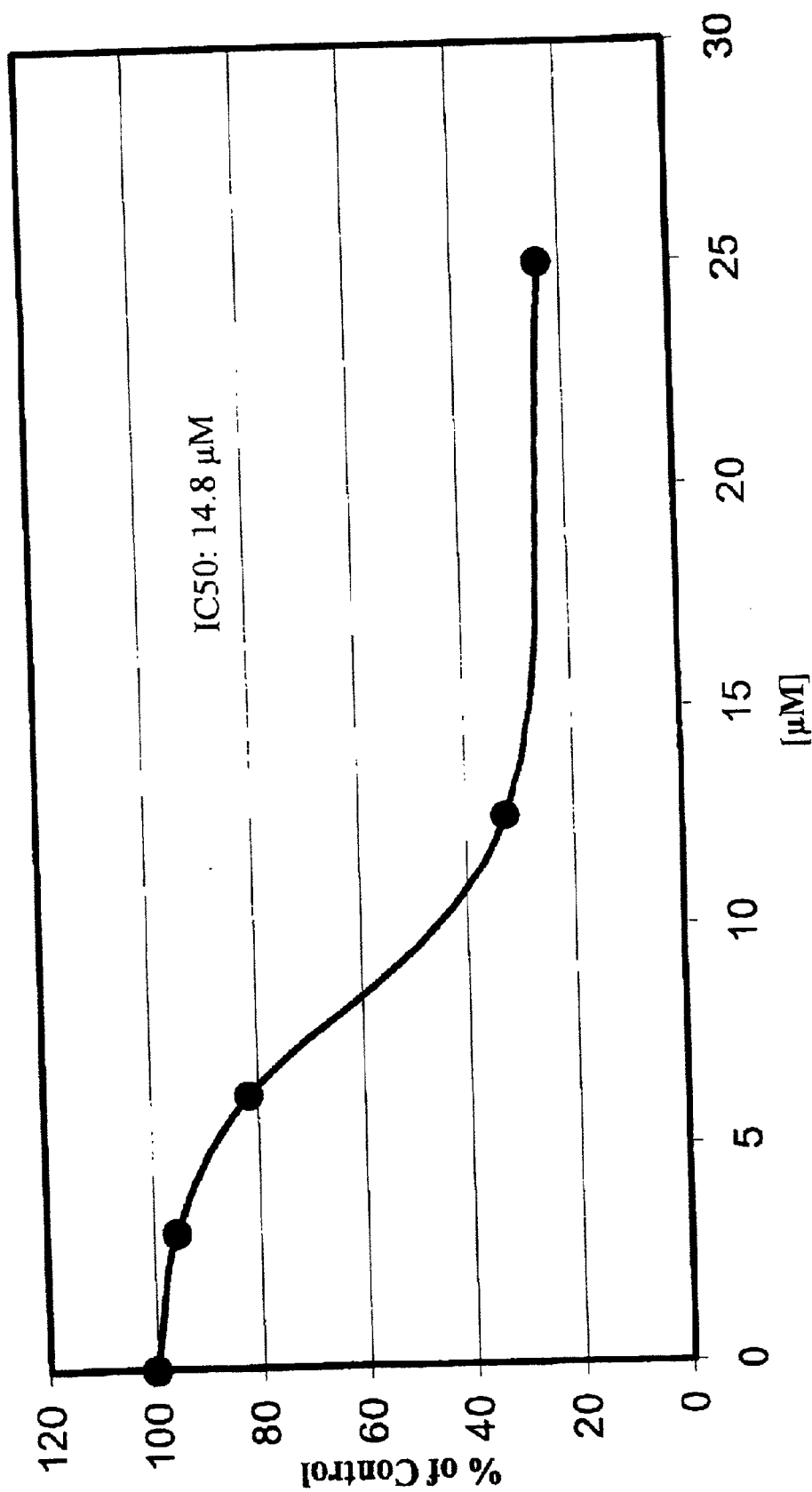
FIG. 18 shows the inhibition of MUC5A/C secretion by MSI-2079.
Figure 19:
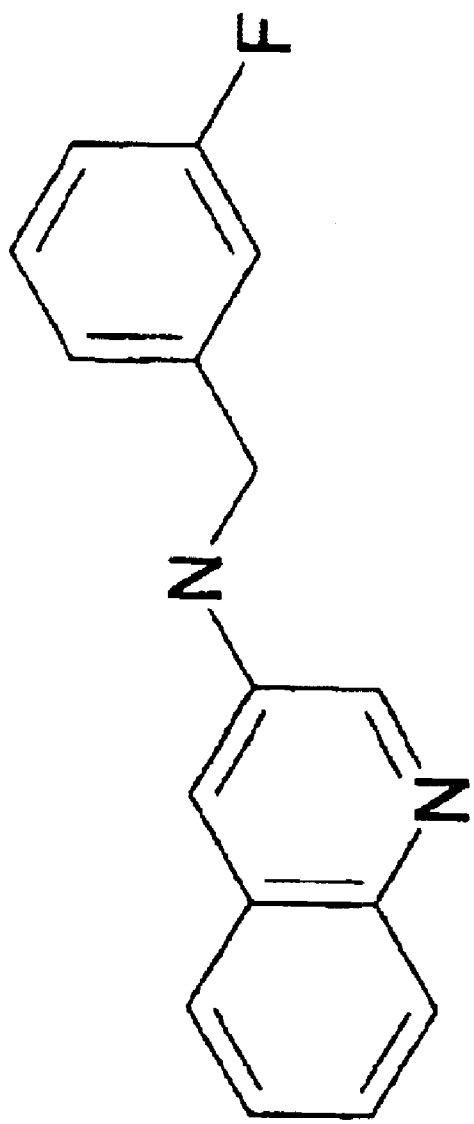
FIG. 19 shows the structure of MSI-2079.

The $IC_{50}$ values for Talniflumate (FIG. 14), Nimesulide (FIG. 17) and MSI-2079 (FIG. 18, the structure of MSI-2079 is shown in FIG. 19) were determined on the basis of its inhibition of MUC5A/C secretion in hCLCA1 expressing H292 cells. Confluent cells were treated with the inhibitor at concentrations from 0 through 250 $\mu$M in OPTI MEM. Secreted MUC5A/C was detected forty-eight hours after addition of the inhibitor by an ELLA assay as described in Example 5. The IC50 values were determined with the data analyzing software GraphPad Prism. The insert of FIG. 14 shows the intracellular mucin levels in response to Talniflumate treatment detected by PAS staining.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. All patents, patent applications and other references cited throughout this application are herein incorporated by reference in their entirety.

REFERENCES

The following references are herein incorporated by reference in their entirety, as are all references, patents or patent applications referred to in this application:

Aikawa T, Shimura S, Sasaki H, Ebina M and Takishima T. Marked goblet cell hyperplasic with mucus accumulation in the airways of patients who died of severe acute asthma attack. Chest, 101, 916–21, 1992.

Alexander A G, Barnes N C and Kay A B. Trial of cyclosporin in corticosteroid-dependent chronic severe asthma. Lancet 339, 324–328, 1992.

Basle, R., Roche, W. R., Roberts, J. A., and Holgate, S. T. Cellular events in the bronchi in mild asthma and after bronchial provocation. Am Rev Respir Dis 139, 806–17, 1989.

Borchers M T, Wesselkamper S, Wert S E, Shapiro S D and Leikauf G D. Monocyte inflammation augments acrolein-induced Muc5ac expression in mouse lung. Am J Physiol, 277(3 Pt 1), L489–97, 1999.

Bosque, J., Chanez, P., Lacoste, J. Y., Barneon, G., Ghavanian, N., Enander, I., Venge, P., Ahlstedt, S., Simony-Lafontaine, J., Godard, P., and et al. Eosinophilic inflammation in asthma [see comments]. N Engl J Med 323, 1033–9, 1990.

Burrows B, Sears M R, Flannery E M, Herbison G P and Holdaway M D. Relationship of bronchial responsiveness assessed by methacholine to serum IgE, lung function, symptoms and diagnoses in 11-year-old New Zealand children. J. Allergy Clin. Immunol. 90, 376–385, 1992.

Burrows B, Martinez F D, Halonen M, Barbee R A and Cline M G. Association of asthma with serum IgE levels and skin-test reactivity to allergens. New Eng. J. Med. 320, 271–277, 1989.

Cardell B S and Pearson R S B. Death in asthmatics. Thorax 14, 341–52, 1959.

Chu J W and Sharom F J. Glycophorin A interacts with interleukin-2 and inhibits interleukin-2-dependent T-lymphocyte proliferation. Cell. Immunol. 145, 223–239, 1992.

Clifford R D, Pugsley A, Radford M and Holgate S T. Symptoms, atopy and bronchial response to methacholine in parents with asthma and their children. Arch. Dis. Childhood 62, 66–73, 1987.

Cutz E, Levison H and Cooper DM. Ultrastructure of airways in children with asthma. Histopathology, 2, 407–21, 1978.

Dugas B, Renauld J C, Pene J, Bonnefoy J, Peti-Frere C, Braquet P, Bosque J, Van Snick J, Mencia-Huerta J M. Interleukin-9 potentiates the interleukin-4-induced immunoglobulin (IgG, IgM and IgE) production by normal human B lymphocytes. Eur. J. Immunol. 23, 1687–1692, 1993.

Dunnill M S. The pathology of asthma, with special reference to changes in the bronchial mucosa. J Clin Invest, 13, 27–33, 1960.

Dunnill M S, Massarella G R and Anderson J A. A comparison of the quantitative anatomy of the bronchi in normal subjects, in asthmaticus, in chronic bronchitis, and in emphysema. Thorax, 24, 176–9, 1969.

Eklund K K, Ghildyal N, Austen K F and Stevens R L. Induction by IL-9 and suppression by IL-3 and IL-4 of the levels of chromosome 14-derived transcripts that encode late-expressed mouse mast cell proteases. J. Immunol. 151, 4266–4273, 1993.

Eng P A, Morton J, Douglass J A, Riedler J, Wilson J and Robertson C F. Short-term efficacy of ultrasonically nebulized hypertonic saline in cystic fibrosis. Pediatr Pulmonol. 21, 77–83, 1996.

Earle B V. Fatal bronchial asthma. Thorax 8, 195–206, 1953.

Ewart S, Levitt R C and Mitzner W. Respiratory system mechanics in mice measured by end-inflation occlusion. J. Appl. Phys. 79, 560–566, 1995.

Gergen P J and Weiss K B. The increasing problem of asthma in the United States. Am. Rev. Respir. Dis. 146, 823–824, 1992.

Gergen P J. The association of allergen skin test reactivity and respiratory disease among whites in the U.S. population. Arch. Intern. Med. 151. 487–492, 1991.

Glynn A A and Michaels L. Bronchial biopsy in chronic bronchitis and asthma. Thorax, 15, 142–53, 1960.

Holgate, S. T., Lackie, P. M., Davies, D. E., Roche, W. R., and Walls, A. F. The bronchial epithelium as a key regulator of airway inflammation and remodeling in asthma. Clin Exp Allergy 29 Suppl 2, 90–5, 1999.

Halonen M, Stern D, Taussig L M, Wright A, Ray C G and Martinez F D. The predictive relationship between serum IgE levels at birth and subsequent incidences of lower respiratory illnesses and eczema in infants. Am. Rev. Respir. Dis. 146, 666–670, 1992.

Jeffery P K. Morphology of the airway wall in asthma and in chronic obstructive pulmonary disease. Am Rev Respir Dis, 143, 1152–8, 1991.

Kleeberger S R, Bassett D J, Jakab G J and Levitt R C. A genetic model for evaluation of susceptibility to ozone-induced inflammation. Am. J. Physiol. 258, L313–320, 1990.

Levitt R C and Ewart S L. Genetic susceptibility to atracurium-induced bronchoconstriction. Am. J. Respir. Crit. Care. Med. 151, 1537–1542, 1995.

Levitt R C. Understanding biological variability in susceptibility to respiratory disease. Pharmacogenetics 1, 94–97, 1991.

Levitt R C and Mitzner W. Autosomal recessive inheritance of airway hyper-reactivity to 5-hydroxytryptamine. J. Appl. Physiol. 67, 1125–1132, 1989.

Levitt R C, Mitzner W et al. Expression of airway hyper-reactivity to acetylcholine as a simple autosomal recessive trait in mice. FASEB J. 2, 2605–2608, 1988.

Louahed J, Kermouni A, Van Snick J and Renauld J C. IL-9 induces expression of granzymes and high affinity IgE receptor in murine T. helper clones. J. Immunol. 154, 5061–5070, 1995.

Louahed J, Toda M, Jen J, Hamid Q, Renauld J C, Levitt R C and Nicolaides N C. Interleukin-9 up-regulates mucus expression in the airways. Accepted in The American Journal of Respiratory Cell and Molecular Biology, Dec. 21, 1999.

Marsh D G, Meyers D A and Bias W B. The epidemiology and genetics of atopic allergy. New Eng. J. Med. 305, 1551–1559, 1982.

Molinoff P et al., Goodman and Gilman's The Pharmacologic Basis of Therapeutics, MacMillan Publishing Company, New York N.Y., 1995.

McLane M P, Tepper J, Weiss C, Tomer Y, Taylor R E, Tumas D, Zhou Y, Haczku A, Nicolaides N C and Levitt, R C. Lung delivery of an Interleukin-9 antibody treatment inhibits airway hyper-responsiveness (AHR), BAL eosinophilia, mucin production and serum IgE elevation to natural antigens in a murine model of asthma. Abstract for AAAAI meeting: Mar. 3-Mar. 8, 2000 in San Diego, Calif. and for ATS/ALA meeting: May 5, 2000 in Toronto, Canada.

Paillasse, R. The relationship between airway inflammation and bronchial hyperresponsiveness. Clin Exp Allergy 19, 395–8, 1989.

Petit-Frere C, Dugas B, Braquet P, Mencia-Huerta J M. Interleukin-9 potentiates the interleukin-4-induced IgE and IgG1 release from murine B lymphocytes. Immunology 79, 146–151, 1993.

Polito, A. J., and Proud, D. Epithelia cells as regulators of airway inflammation. J Allergy Clin Immunol 102, 714–8, 1998:

Salvato G. Some histologic changes in chronic bronchitis and asthma. Thorax, 23, 168–72, 1968.

Sears M R, Burrows B, Flannery E M, Herbison G P, Hewitt C J and Holdaway M D. Relation between airway responsiveness and serum IgE in children with asthma and in apparently normal children. New Engl. J. Med. 325(15), 1067–1071, 1991.

Takahashi K, Mizuno H, Ohno H, Kai H, Isohama Y, Takahama K, Nagaoka and Miyata T. Effects of SS320A, a new cysteine derivative, on the change in the number of goblet cells induced by isoproterenol in rat tracheal epithelium. Jpn J Pharmacol, 77, 71–77, 1998.

Takizawa, H. Airway epithelial cells-as regulators of airway inflammation (Review). Int J Mol Med 1, 367–78, 1998.

Temann, U. A., Geba, G. P., Rankin, J. A., and Flavell, R. A. Expression of interleukin 9 in the lungs of transgenic mice causes airway inflammation, mast cell hyperplasia, and bronchial hyperresponsiveness. J Exp Med 188, 1307–20, 1998.

Voynow J A and Rose M C. Quantitation of mucin mRNA in respiratory and intestinal epithelial cells. Am J Respir Cell Mol Biol, 11, 742–750, 1994.

Voynow J A, Young L R, Wang Y, Horger T, Rose M C and Fischer B M. Neutrophil elastase increases MUC5AC mRNA and protein expression in respiratory epithelial cells. Am J Physiol, 276(5 Pt 1), L835–43, 1999.

What is claimed is:

1. A method of treating a subject with a disease characterized by the production of mucin, comprising administering to the subject an effective amount of a composition comprising a 2-aminophenyl acetic acid compound or a pharmaceutically acceptable salt thereof.

2. A method of claim 1, wherein the disease is selected from the group consisting of a chronic obstructive pulmonary disease (COPD), an inflammatory lung disease, and an acute or chronic infectious disease.

3. A method of claim 1, wherein the mucin production occurs in the respiratory tract of the subject.

4. A method of claim 1, wherein the mucin production occurs in the gastrointestinal tract of the subject.

5. A method of claim 4, wherein the mucin production occurs in the pancreas of the subject.

6. A method of claim 2, wherein the disease is asthma.

7. A method of claim 2, wherein the disease is bronchitis.

8. A method of claim 2, wherein the disease is chronic bronchitis.

9. A method of claim 2, wherein the disease is cystic fibrosis.

10. A method of claim 2, wherein the disease is emphysema.

11. A method of claim 2, wherein the disease is gastrointestinal malabsorption syndrome.

12. A method of claim 2, wherein the disease is steatorrhea.

13. A method of claim 2, wherein the disease is diarrhea.

14. A method of claim 2, wherein the disease is allergic inflammation.

15. A method of claim 2, wherein the treatment reduces airway inflammation.

16. A method of claim 2, wherein the treatment reduces inflammatory cells.

17. A method of claim 2, wherein the treatment reduces epithelial-related inflammation.

18. A method of claim 1, wherein the treatment is for bronchial hyperresponsiveness.

19. A method of claim 1, wherein the treatment downregulates mediators of airway inflammation.

20. A method of claim 19, wherein the mediator is a chemokine.

21. A method of claim 19, wherein the mediator is a cytokine.

22. A method of claim 20, wherein the cytokine is interleukin 9.

23. A method of claim 1, wherein the treatment decreases the number of goblet cells in the respiratory tract.

24. A method of claim 1, wherein the treatment decreases the number of goblet cells in the gastrointestinal tract.

25. A method of claim 1, wherein the treatment decreases the number of submucosal glands in the respiratory tract.

26. A method of claim 1, wherein the treatment decreases the number of submucosal glands in the gastrointestinal tract.

27. A method of claim 1, wherein the 2-amino phenylacetic acid compound is talniflumate or a pharmaceutically acceptable salt thereof.

28. A method of claim 27, wherein the composition consists essentially of talniflumate.

29. A method of claim 1, wherein the 2-aminophenyl acetic acid compound is formulated as a prodrug.

30. A method of claim 1, wherein the 2-aminophenyl acetic acid compound inhibits chloride channel activity.

31. A method of claim 30, wherein the chloride channel is a calcium activated chloride channel.

32. A method of claim 31, wherein the calcium activated chloride channel is human CLCA1 or CLCA2.

33. A method of claim 30, wherein the 2-aminophenyl acetic acid compound is talniflumate.

34. A method of claim 1, wherein the composition is administered by a systemic route.

35. A method of claim 34, wherein the composition is administered by a parenteral route.

36. A method of claim 35, wherein the parenteral route is selected from the group consisting of intravenous, intramuscular, intraperitoneal and subcutaneous administration.

37. A method of claim 15, wherein the composition is formulated as a suppository for subcutaneous or intramuscular injection.

38. A method of claim 1, wherein the composition is administered by an oral route.

39. A method of claim 38, wherein the composition is formulated for oral administration in a formulation selected from the group consisting of capsules, tablets, elixirs, suspensions and syrups.

40. A method of claim 38, wherein the composition is formulated as a controlled release formulation.

41. A method of claim 1, wherein the composition further comprises a pharmaceutically acceptable carrier.

42. A method of claim 41, wherein the pharmaceutically acceptable carrier is selected from the group consisting of a surfactant, stabilizing agent, encapsulating agents, and absorption-enhancing agent.

43. A method of claim 41, wherein the pharmaceutically acceptable carrier is sterile water or sterile oil.

44. A method of claim 42, wherein the sterile oil is selected from the group consisting of petroleum, animal, vegetable, peanut, soybean, mineral and sesame oil.

45. A method of claim 41, wherein the pharmaceutically acceptable carrier is selected from the group consisting of saline, glycerol and dextrose solutions.

46. A method of claim 1, wherein the composition is administered by inhalation.

47. A method of claim 46, wherein the composition is in the form of an aerosol.

48. A method of claim 1, wherein the composition is administered by an inhaler.

49. A method of claim 48, wherein the inhaler is a metered dose inhaler.

50. A method of claim 48, wherein the inhaler is a dry powder inhaler.

51. A method of claim 1, wherein the composition is administered in a topical formation as a solution, suspension, gel, ointment or salve.

52. A method of claim 1, wherein the composition is administered in combination with a second agent for the treatment of any of the diseases listed in claims 6 to 14.

53. A method of claim 52, wherein the second agent is selected from the group consisting of expectorants, mucolytics, antibiotics, antihistamines, steroids, anti-inflammatory agents, and decongestants.

54. A method of claim 52, wherein the second agent is a beta receptor agonist.

55. A method of claim 52, wherein the second agent is a steroid.

56. A method of claim 52, wherein the second agent is a leukotriene antagonist.

57. A method of treating a subject with a disease characterized by the production of mucin, comprising administering to the subject an effective amount of a composition comprising talniflumate or a pharmaceutically acceptable salt thereof.

58. A method of treating cystic fibrosis in a subject in need of such treatment comprising administering to the subject an effective amount of a composition comprising talniflumate or a pharmaceutically acceptable salt thereof.

59. A method of treating cystic fibrosis in a subject in need of such treatment comprising administering to the subject an effective amount of a composition consisting essentially of talniflumate or a pharmaceutically acceptable salt thereof.

* * * * *